United States Patent
Akcan et al.

(10) Patent No.: US 12,053,464 B2
(45) Date of Patent: Aug. 6, 2024

(54) PHARMACEUTICAL DOSAGE FORMS

(71) Applicant: Purdue Pharma L.P., Stamford, CT (US)

(72) Inventors: Ozgur Akcan, Parlin, NJ (US);
Stephen Harris, Weston, CT (US);
Richard Mannion, Furlong, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 16/755,371

(22) PCT Filed: Oct. 19, 2018

(86) PCT No.: PCT/US2018/056724
§ 371 (c)(1),
(2) Date: Apr. 10, 2020

(87) PCT Pub. No.: WO2019/079729
PCT Pub. Date: Apr. 25, 2019

(65) Prior Publication Data
US 2021/0205295 A1    Jul. 8, 2021

Related U.S. Application Data

(60) Provisional application No. 62/574,978, filed on Oct. 20, 2017.

(51) Int. Cl.
*A61K 31/485* (2006.01)
*A61K 9/20* (2006.01)
*A61K 9/28* (2006.01)

(52) U.S. Cl.
CPC .......... *A61K 31/485* (2013.01); *A61K 9/2013* (2013.01); *A61K 9/2031* (2013.01); *A61K 9/2095* (2013.01); *A61K 9/2853* (2013.01); *A61K 9/2893* (2013.01)

(58) Field of Classification Search
CPC .. A61K 31/485; A61K 9/2013; A61K 9/2031; A61K 9/2095; A61K 9/2853; A61K 9/2893
See application file for complete search history.

(56) References Cited

U.S. PATENT DOCUMENTS

| | | | | |
|---|---|---|---|---|
| 4,486,436 A * | 12/1984 | Sunshine | ............... | A61K 31/54 514/263.31 |
| 5,286,493 A * | 2/1994 | Oshlack | ............... | A61K 9/5078 424/483 |
| 5,472,712 A * | 12/1995 | Oshlack | ............... | A61K 9/2866 427/372.2 |
| 5,914,129 A * | 6/1999 | Mauskop | ............... | A61K 45/06 424/464 |
| 7,736,667 B2 * | 6/2010 | Berner | ............... | A61K 9/2866 424/457 |
| 7,842,309 B2 * | 11/2010 | Oshlack | ............... | A61K 9/2077 424/464 |
| 8,563,038 B2 * | 10/2013 | Andersen | ............ | A61K 31/485 424/486 |
| 8,808,740 B2 * | 8/2014 | Huang | ................. | A61K 9/2031 424/469 |
| 8,901,175 B2 * | 12/2014 | Miltner | ................... | A61P 35/00 514/648 |
| 8,945,619 B2 * | 2/2015 | Berner | ................. | A61K 31/525 424/468 |
| 9,114,071 B2 * | 8/2015 | Coulter | .................... | A61P 1/10 |
| 9,744,136 B2 * | 8/2017 | Huang | ................ | A61K 9/2077 |
| 10,238,608 B2 * | 3/2019 | Davey | ................. | A61K 9/0024 |
| 2005/0074493 A1 * | 4/2005 | Mehta | ................. | A61K 9/5084 514/282 |
| 2011/0097395 A1 * | 4/2011 | Babul | ..................... | A61P 25/36 424/490 |
| 2012/0178771 A1 * | 7/2012 | Babul | ................. | A61K 9/2054 514/282 |
| 2014/0186437 A1 * | 7/2014 | Schoenhard | .......... | A61K 31/00 424/452 |

(Continued)

FOREIGN PATENT DOCUMENTS

| | | |
|---|---|---|
| JP | 2017211168 A | 11/2017 |
| WO | 2005065673 A1 | 7/2005 |
| WO | 2008023261 A1 | 2/2008 |
| WO | 2012085656 A2 | 6/2012 |
| WO | 2013038267 A1 | 3/2013 |

(Continued)

OTHER PUBLICATIONS

International Search Report for International Application No. PCT/US2018/056724 mailed Dec. 21, 2018, 2 pgs.

(Continued)

*Primary Examiner* — Robert A Wax
*Assistant Examiner* — Olga V. Tcherkasskaya
(74) *Attorney, Agent, or Firm* — LOWENSTEIN SANDLER LLP

(57) ABSTRACT

The invention relates to a solid dosage form comprising a core-shell structure comprising two or more different active agents, wherein the core-shell structure comprises (1) a core comprising a first matrix formulation, the first matrix formulation comprising at least one active agent selected from the group of an active agent (A) and an active agent (B); and (2) a shell encasing the core and comprising a second matrix formulation, wherein the weight ratio of the first matrix formulation to the second matrix formulation is from about 1:10 to about 4:1. In certain embodiments, the solid dosage forms of the invention are in oral solid extended release dosage forms, which provide an extended release of at least a portion of at least one active agent included therein.

13 Claims, 10 Drawing Sheets

(56) References Cited

U.S. PATENT DOCUMENTS

| | | |
|---|---|---|
| 2014/0193490 A1 | 7/2014 | Schoenhard |
| 2016/0176890 A1* | 6/2016 | Babul ................ A61K 9/5078 |
| | | 514/282 |
| 2016/0243107 A1 | 8/2016 | Moline |
| 2017/0000783 A1 | 1/2017 | Devane et al. |
| 2017/0172930 A1* | 6/2017 | Berner .................. A61P 31/00 |
| 2019/0054024 A1* | 2/2019 | Yang ................... A61K 9/2031 |

FOREIGN PATENT DOCUMENTS

| | | |
|---|---|---|
| WO | 2015100197 A1 | 7/2015 |
| WO | 2016040934 A1 | 3/2016 |

OTHER PUBLICATIONS

Office Action for Japanese Patent Application No. 2020-518798 with English translation dated Jun. 28, 2022, 10 pages.

\* cited by examiner

PHARMACEUTICAL DOSAGE FORMS

CROSS REFERENCE TO RELATED APPLICATION SECTIONS

The present application is a national stage entry under 35 U.S.C. § 371 of International Application No. PCT/US2018/056724 filed on Oct. 19, 2018, which claims priority to U.S. Provisional Patent Application No. 62/574,978 filed on Oct. 20, 2017, the contents of which are incorporated in their entirety.

TECHNICAL FIELD OF THE INVENTION

The invention relates to solid oral dosage forms comprising at least two active agents, which are both released in a controlled manner.

BACKGROUND OF THE INVENTION

Pharmaceutical dosage forms can contain more than one active agent. The development of such dosage forms can be challenging, if a specific extended release profile needs to be tailored for each of the active agents, in order to adjust their pharmacokinetic profiles as needed.

For example, it may be desirable that a first active agent is released rather slowly (e.g., over a period of 12 hours), while a second active agent present in the same dosage form is released also in a controlled manner, but more quickly (e.g., such that the release is complete within a period of 4 hours). Achieving such release characteristics may be particularly demanding, if the first active agent (to be released more slowly) has a significantly higher water solubility than the second active agent, and thus the tendency to be released more quickly. It may likewise be desirable to prepare a dosage form of two active agents with significantly different water solubility such that they exhibit substantially superimposable in vitro release profiles, or to prepare a dosage form of two active agents with the same water solubility, such that they exhibit substantially different in vitro release profiles. These and similar tasks can be subsumed as "independently adjusting" the in vitro release profiles of two active agents from a dosage form.

Another challenge for formulation scientists is that pharmaceutical dosage forms containing active agents, such as opioid analgesics, sometimes are subject to abuse. This is particularly the case for extended release dosage forms containing a higher dose of the active agent, compared to immediate-release products containing lower dose of the active agent.

Opioid products can be abused in a number of ways. For example, they can be swallowed whole, crushed and swallowed, crushed and snorted, crushed and smoked, or crushed, dissolved and injected. Because opioid products are often manipulated for purposes of abuse by different routes of administration or to defeat extended-release properties, most abuse-deterrent technologies developed to date are intended to make manipulation more difficult or to make abuse of the manipulated product less attractive or less rewarding.

There continues to exist a need for pharmaceutical dosage forms which provide an extended release of two or more active agents, wherein the in vitro release profiles of the two active agents are independently adjusted. In particular, there continues to exist a need for such dosage forms that are easy to manufacture, and/or additionally exhibit abuse-deterrent properties, such as a certain minimum hardness which impedes crushing or pulverization of the dosage form.

SUMMARY OF THE INVENTION

In certain embodiments, the invention is directed to a solid oral dosage form providing an extended release of more than one active agent.

In certain embodiments, the invention is directed to a solid oral dosage form providing an extended release of two active agents, wherein the in vitro release profiles of the two active agents are independently adjusted.

In certain embodiments, the invention is directed to a method of adjusting the in vitro release profiles of at least two active agents to be released from a single, solid oral extended release dosage form.

In certain embodiments, the invention is directed to a solid oral extended release dosage form comprising at least two active agents, and having abuse-deterrent properties.

In certain embodiments, the invention is directed to a solid oral extended release dosage form comprising at least two active agents, which exhibits features of impeding crushing or pulverization of the dosage form.

In certain embodiments, the invention is directed to a solid oral extended release dosage form comprising a core-shell structure comprising an active agent (A) and an active agent (B), wherein the core-shell structure comprises
  (1) a core comprising a first matrix formulation, the first matrix formulation comprising at least one active agent selected from active agent (A) and active agent (B); and
  (2) a shell encasing the core and consisting of a second matrix formulation, wherein the weight ratio of the first matrix formulation to the second matrix formulation is from about 1:10 to about 4:1.

In certain embodiments, the invention is directed to a solid oral extended release dosage form as disclosed herein, for use in a method of treating or preventing pain, wherein at least one of active agents, e.g., active agent (A), is an opioid analgesic.

In certain embodiments, the invention is directed to the use of a solid oral extended release dosage form as disclosed herein, for the manufacture of a medicament for treating or preventing pain, wherein at least one of active agents, e.g., active agent (A), is an opioid analgesic.

In certain embodiments, the invention is directed to a method of treating or preventing pain comprising administering to a patient identified in need thereof a solid oral extended release dosage form as disclosed herein, wherein at least one of active agents, e.g., active agent (A), is an opioid analgesic.

In certain embodiments, the invention is directed to the use of a core-shell structure 10 comprising an amount of an active agent (A) and a separate amount of an active agent (B), wherein said core-shell structure comprises
  (1) a core comprising a first matrix formulation, the first matrix formulation comprising at least one active agent selected from active agent (A) and active agent (B); and
  (2) a shell encasing the core and consisting of a second matrix formulation, wherein the weight ratio of the first matrix formulation to the second matrix formulation is from about 1:10 to about 4:1,
in a solid oral extended release dosage form, for independently adjusting the in vitro release profiles of the active agent (A) and the active agent (B) from said dosage form.

In certain embodiments, the invention is directed to a method of independently adjusting the in vitro release profiles of an active agent (A) and an active agent (B) from a solid oral extended release dosage form, comprising
preparing a core-shell structure comprising an amount of the active agent (A) and a separate amount of the active agent (B), wherein the core-shell structure comprises (1) a core comprising a first matrix formulation, and (2) a shell encasing the core and comprising a second matrix formulation,
wherein the weight ratio of the first matrix formulation to the second matrix formulation is from about 1:10 to about 4:1, wherein the amount of active agent (A) is distributed between the first and the second matrix formulation, and the amount of active agent (B) is distributed between the first and the second matrix formulation, such that the first matrix formulation comprises at least one active agent selected from active agent (A) and active agent (B); and
providing said dosage form containing said core-shell structure.

In certain specific embodiments, the dosage form of the invention used herein offer beneficial characteristics, including such as, a reduction of adverse pharmacodynamic responses associated with stand-alone monotherapies. In certain embodiments, the dosage form of the invention is useful for the treatment or prevention of pain. In certain embodiments when opioid analgesics are used as one or both of the active agents in accordance with the invention, it is believed that the dosage forms and methods of treatment thereof of the invention offer effective pain relief with improved features (such as, with reduced abuse potential, or with reduced adverse pharmacodynamic responses), compared to monotherapies where a single opioid agonist is administered.

In describing the invention, the following terms are to be used as indicated below.

As used herein, the singular forms "a", "an", and "the" include plural references unless the context clearly indicates otherwise.

The term "abuse" is defined for purposes of the invention as the intentional, non-therapeutic use of a drug product or substance, even once, to achieve a desirable psychological or physiological effect.

The term "abuse-deterrent properties" is defined for purposes of the invention as those properties shown to meaningfully deter abuse, even if they do not fully prevent abuse.

The term "dosage form" is defined for purposes of the invention as to refer to a pharmaceutical dosage form.

The term "extended release" is defined for purposes of the invention as to refer to the release of a drug (or active agent) from a product (or dosage form) that is formulated to make the active agent (or drug) available over an extended period after ingestion, thereby allowing a reduction in dosing frequency compared to a drug presented as a conventional dosage form (e.g., as a solution or an immediate release dosage form).

The term "controlled release" is defined for purposes of the invention as to refer to the release of a drug (or active agent) at a controlled rate from a product (or dosage form), including such as delayed release. In certain circumstances, "controlled release" means "extended release" as above defined.

The term "immediate release" is defined for purposes of the invention as to refer to the release of a drug (or active agent) from a product (or dosage form) that is formulated to make the active agent (or drug) to dissolve in the gastrointestinal contents with no intention of delaying or prolonging the dissolution or absorption of the drug. In certain embodiments, the term "immediate release" dosage form refers to a dosage form releasing at least about 80%, or at least about 85%, of the active agent(s) within 45 minutes, as measured by in-vitro dissolution in a USP Apparatus 1 (basket) at 100 rpm in 900 ml simulated gastric fluid without enzymes (SGF) at 37.0±0.5° C.

In certain embodiments of the invention, the term "extended release dosage form" refers to a dosage form releasing less than about 80%, or less about 75%, of each of the active agent(s) contained therein within 45 minutes, as measured by in-vitro dissolution in a USP Apparatus 1 (basket) at 100 rpm in 900 ml simulated gastric fluid without enzymes (SGF) at 37.0±0.5° C. In certain embodiments, the term "extended release dosage form" refers to a dosage form releasing less than about 80%, or less than about 75%, of each of the active agent(s) contained therein within 45 minutes, as measured by in-vitro dissolution in a USP Apparatus 1 (basket) at 100 rpm in 900 ml simulated gastric fluid without enzymes (SGF) at 37.0±0.5° C.

The term "solid oral extended release dosage form" refers to the pharmaceutical dosage form comprising a unit dose of the active agents (i.e., of active agent (A) and active agent (B)), in which at least a portion of at least one active agent is released in the extended manner after ingestion. The unit dose of active agent (A) and active agent (B) is partially or even completely contained in the core-shell structure as described herein. The dosage form can comprise one core-shell structure (e.g., if the core-shell structure is in tablet form), or more than one core-shell structure (e.g., if the core-shell structure is in the form of beads, spheres, pellets, minitablets or multiparticulates). The dosage form can optionally further contain other excipients, adjuvants and additives conventional in the art, or any other additional features or components that can be used in a pharmaceutical dosage form, such as a protective (or cosmetic) coating. The extended release pharmaceutical dosage form can be, for instance, a tablet comprising the core-shell structure(s), or a capsule comprising the core-shell structures in the form of beads or multiparticulates.

The "solid oral extended release dosage form" of the invention may comprise a portion of at least one of the active agents in extended release form, and another portion of the at least one active agent in immediate release form, e.g., as an immediate release layer of the active agent(s) surrounding the dosage form, or an immediate release component included within the dosage form (e.g., as a further "immediate release" layer encasing the shell of the core-shell structure). Alternatively, the "solid oral extended release dosage form" of the invention may comprise one of the active agents in the extended release form, and the other active agent(s) is in the immediate release form. In other embodiments, the "solid oral extended release dosage form" of the invention may comprise a portion of each of the active agents in the extended release form, and another portion of each of the active agents is in the immediate release form. In still another embodiment, the active agents are all present in the extended release form in the "solid oral extended release dosage form" of the invention. In further separate embodiments, the "solid oral extended release dosage form" of the invention may comprise a portion of one active agent in the extended release form, and the remaining portion of said active agent (together with all the amount of the other active agent) is in the immediate release form. In certain embodiments, a "solid oral extended release pharmaceutical dosage form" according to the invention can be provided once daily or twice daily in a dosing regimen.

For purposes of the invention, the term "solid oral extended release pharmaceutical dosage form" does not encompass dosage forms using OROS® (Osmotic Controlled Release Oral Delivery System) technology. Therefore the "solid oral extended release dosage form" preferably excludes dosage forms that include a semipermeable coating. However, the "solid oral extended release pharmaceutical dosage form" can include for example a cosmetic film coating which is coated, e.g., onto the core-shell structure(s) of the dosage form.

The term "first matrix formulation" is defined for purposes of the invention as a shaped solid form of a composition comprising at least one active agent (i.e., at least one active agent selected from active agent (A) and active agent (B)), and at least one extended release feature such as an extended release matrix material, such as, polyethylene oxides, alkylcelluloses, cellulose ethers, waxes, shellacs, gums, acrylic resins, poly acrylates, polymethacrylates, in particular polyethylene oxide. The composition can optionally comprise further compounds, namely further active agents and additional retardants and/or other materials, including but not limited to, adjuvants and additives conventional in the art, such as lubricants.

For purposes of the invention, the term "first matrix formulation" refers to an extended release matrix formulation, which provides an extended release of the active agent(s) contained therein (i.e., active agent (A) and/or active agent (B)), even in the absence of the shell encasing the core. Thus, in certain embodiments, the first matrix formulation releases less than about 80%, or less about 75%, of each active agent contained therein within 45 minutes, as measured by in-vitro dissolution in a USP Apparatus 1 (basket) at 100 rpm in 900 ml simulated gastric fluid without enzymes (SGF) at 37.0±0.5° C. In certain embodiments, the first matrix formulation releases less than about 80%, or less than about 75%, of each active agent contained therein within 1 hour, as measured by in-vitro dissolution in a USP Apparatus 1 (basket) at 100 rpm in 900 ml simulated gastric fluid without enzymes (SGF) at 37.0±0.5° C.

For purposes of the invention, the term "second matrix formulation" can have two meanings (i.e., alternative (i) and alternative (ii)).

According to alternative (i), the term "second matrix formulation" is defined as a composition comprising at least one active agent (i.e., at least one active agent selected from active agent (A) and active agent (B)), and at least one matrix material(s) (e.g., an immediate release matrix material or an extended release matrix material) in which the at least one active agent is dispersed or embedded. In certain embodiments, at least one matrix material(s) is an extended release matrix material, including such as, polyethylene oxides, alkylcelluloses, cellulose ethers, waxes, shellacs, gums, acrylic resins, polyacrylates, polymethacrylates). In a certain embodiment, the matrix material(s) comprise polyethylene oxide. The composition can optionally comprise further compounds, namely further active agents and additional retardants and/or other materials, including but not limited to, adjuvants and additives conventional in the art, such as lubricants. According to this alternative, the term "second matrix formulation" refers to an extended release matrix formulation, which provides an extended release of the active agent(s) contained therein (i.e., active agent (A) and/or active agent (B)). Thus, in certain embodiments, the second matrix formulation releases less than about 80%, or less about 75%, of each active agent contained therein within 45 minutes, as measured by in-vitro dissolution in a USP Apparatus 1 (basket) at 100 rpm in 900 ml simulated gastric fluid without enzymes (SGF) at 37.0±0.5° C. In certain embodiments, the second matrix formulation releases less 25 than about 80%, or less than about 75%, of each active agent contained therein within 1 hour, as measured by in-vitro dissolution in a USP Apparatus 1 (basket) at 100 rpm in 900 ml simulated gastric fluid without enzymes (SGF) at 37.0±0.5° C.

According to alternative (ii), the term "second matrix formulation" is defined as a composition comprising at least one matrix material, such as, polyethylene oxides, alkylcelluloses, cellulose ethers, waxes, shellacs, gums, acrylic resins, polyacrylates, polymethacrylates. In one embodiment, the second matrix formulation comprises an extended release material, such as, polyethylene oxide. The composition can optionally comprise further compounds, namely additional retardants and/or other materials, including but not limited to, adjuvants and additives conventional in the art, such as lubricants, but is free of the active agents (i.e., neither active agent (A) nor active agent (B) is included). According to this alternative, the second matrix formulation serves to control the release of the active agents contained in the first matrix formulation.

To determine whether the first matrix formulation and/or the second matrix formulation of a given core-shell structure provide a desired release profile of the active agent(s) contained therein, the following procedure may be applied:

To determine the release profile of the first matrix formulation, test cores corresponding to the cores of the given core-shell structure (i.e., having inter alia the same composition, weight and dimensions) are prepared and these test cores (without shell) are subjected to the in vitro dissolution test.

To determine the release profile of the second matrix formulation, test core-shell structures are prepared and subjected to the in vitro dissolution test. The test core-shell structures correspond to the given core-shell structure (i.e., have inter alia the same composition, weight and dimensions of the core and of the shell), except that in the core, the active agents are omitted and replaced by the same amount of matrix material ("dummy core").

For purposes of the invention, the expression "matrix formulation comprising an active agent" means that the respective active agent is embedded in the matrix formulation, e.g., in the form of a solid solution, dispersion, or molecular dispersion of the active agent in the matrix formulation.

For purposes of the invention, the expression "shell encasing the core" means that at least 95%, at least 97%, or 100% of the surface of the core are surrounded by the shell, wherein the first matrix formulation of the core and the second matrix formulation of the shell can either be in direct contact, or separated by an intermediate layer or coating. In certain embodiments, the first matrix formulation of the core and the second matrix formulation of the shell are in direct contact.

For purposes of the invention, the "shell" consisting of the second matrix formulation does not necessarily represent the outermost layer of the "core-shell structure". Thus, in certain embodiments, the core-shell structure comprises, in addition to the core and the shell encasing the core, one or more additional layers encasing the shell. For example, an additional layer can consist of a third matrix formulation, wherein the term "third matrix formulation" can have analogous meanings as described herein for the term "second matrix formulation". An additional layer can also be a formulation comprising an amount of active agent (A)

and/or an amount of active agent (B), which provides an immediate release of the active agents contained therein (as long as the overall dosage form still provides an extended release of the active agents (A) and (B)). An additional layer can also be a protective or cosmetic coating, or a taste-masking coating.

The term "simulated gastric fluid" or "SGF" used herein refers to an aqueous solution utilized in dissolution testing to mimic the conditions of the stomach, e.g., a solution of 0.1 N HCl.

The term "USP Apparatus 1 (basket)" refers to the Apparatus 1 (Basket Apparatus) described in U.S. Pharmacopoeia 39 (2016) (see, in particular, Section <711> Dissolution). The term "in-vitro dissolution test in a USP Apparatus 1 (basket)" refers to the respective method using the Apparatus 1 (basket) as described in U.S. Pharmacopoeia 39 (2016) (see, in particular Section <711> Dissolution).

For purposes of the invention, the "in-vitro dissolution test in a USP Apparatus 1 (basket)" is used in a slightly modified form, by equipping the USP Apparatus 1 basket with a retaining spring placed in the upper part of the basket (above the tablet), to reduce the propensity of the polyethylene oxide containing tablets, once hydrated in the dissolution medium, to stick to the solid underside of the top of the basket or the base of the shaft. For example, a passivized stainless steel 316 spring, 1.5-cm outside diameter and 2-cm length can be used.

The term "polyethylene oxide" ("PEO") is defined for purposes of the invention as having an approximate molecular weight of at least 25,000 g/mol, and preferably as having an approximate molecular weight of at least 100,000 g/mol, measured as is conventional in the art, and preferably measured based on rheological measurements as described further below. Compositions with lower approximate molecular weight are usually referred to as polyethylene glycols.

For purposes of the invention, the approximate molecular weight of a polyethylene oxide is determined based on rheological measurements. Since polyethylene oxides are polydisperse polymers, the approximate molecular weight of a polyethylene oxide (determined based on rheological measurements) corresponds to an average molecular weight.

For purposes of the invention, a polyethylene oxide having a certain approximate molecular weight (determined based on rheological measurements) can be a single grade of a (commercially available) polyethylene oxide, or a mixture or blend of two or more grades.

The approximate molecular weight of a polyethylene oxide (either single grade or mixture of grades), is determined based on rheological measurements, as follows:

Polyethylene oxide is considered to have an approximate molecular weight of 100,000 g/mol when a 5% (by weight) aqueous solution of said polyethylene oxide using a Brookfield viscometer Model RVT, spindle No. 1, at 50 rpm, at 25° C. shows a viscosity range of 30 to 50 mPa s (cP);

Polyethylene oxide is considered to have an approximate molecular weight of 200,000 g/mol when a 5% (by weight) aqueous solution of said polyethylene oxide using a Brookfield viscometer Model RVT, spindle No. 1, at 50 rpm, at 25° C. shows a viscosity range of 55 to 90 mPa s (cP);

Polyethylene oxide is considered to have an approximate molecular weight of 300,000 g/mol when a 5% (by weight) aqueous solution of said polyethylene oxide using a Brookfield viscometer Model RVF, spindle No. 1, at 10 rpm, at 25° C. shows a viscosity range of 600 to 1,200 mPa s (cP);

Polyethylene oxide is considered to have an approximate molecular weight of 600,000 g/mol when a 5% (by weight) aqueous solution of said polyethylene oxide using a Brookfield viscometer Model RVF, spindle No. 2, at 2 rpm, at 25° C. shows a viscosity range of 4,500 to 8,800 mPa s (cP);

Polyethylene oxide is considered to have an approximate molecular weight of 900,000 g/mol when a 5% (by weight) aqueous solution of said polyethylene oxide using a Brookfield viscometer Model RVF, spindle No. 2, at 2 rpm, at 25° C. shows a viscosity range of 8,800 to 17,600 mPa s (cP);

Polyethylene oxide is considered to have an approximate molecular weight of 1,000,000 g/mol when a 2% (by weight) aqueous solution of said polyethylene oxide using a Brookfield viscometer Model RVF, spindle No. 1, at 10 rpm, at 25° C. shows a viscosity range of 400 to 800 mPa s (cP);

Polyethylene oxide is considered to have an approximate molecular weight of 2,000,000 g/mol when a 2% (by weight) aqueous solution of said polyethylene oxide using a Brookfield viscometer Model RVF, spindle No. 3, at 10 rpm, at 25° C. shows a viscosity range of 2,000 to 4,000 mPa s (cP);

Polyethylene oxide is considered to have an approximate molecular weight of 4,000,000 g/mol when a 1% (by weight) aqueous solution of said polyethylene oxide using a Brookfield viscometer Model RVF, spindle No. 2, at 2 rpm, at 25° C. shows a viscosity range of 1,650 to 5,500 mPa s (cP);

Polyethylene oxide is considered to have an approximate molecular weight of 5,000,000 g/mol when a 1% (by weight) aqueous solution of said polyethylene oxide using a Brookfield viscometer Model RVF, spindle No. 2, at 2 rpm, at 25° C. shows a viscosity range of 5,500 to 7,500 mPa s (cP);

Polyethylene oxide is considered to have an approximate molecular weight of 7,000,000 g/mol when a 1% (by weight) aqueous solution of said polyethylene oxide using a Brookfield viscometer Model RVF, spindle No. 2, at 2 rpm, at 25° C. shows a viscosity range of 7,500 to 10,000 mPa s (cP);

Polyethylene oxide is considered to have an approximate molecular weight of 8,000,000 g/mol when a 1% (by weight) aqueous solution of said polyethylene oxide using a Brookfield viscometer Model RVF, spindle No. 2, at 2 rpm, at 25° C. shows a viscosity range of 10,000 to 15,000 mPa s (cP).

In certain embodiments, when a matrix formulation contains two or more grades of polyethylene oxide, either the entire mixture of the polyethylene oxide grades contained therein, or a subgroup thereof (including only a single polyethylene oxide grade) meets the definition of a given approximate molecular weight (or approximate molecular weight range), determined based on rheological measurements.

For purposes of the invention, a polyethylene oxide (either a single grade or a mixture of grades) meeting two or more criteria of the above rheological tests, is assigned the respective higher approximate molecular weight. For example, a polyethylene oxide which, in a 1% (by weight) aqueous solution of said polyethylene oxide using a Brookfield viscometer Model RVF, spindle No. 2, at 2 rpm, at 25° C., shows a viscosity of 5,500 mPa s (cP), which is the threshold value between an approximate molecular weight of 4,000,000 g/mol and 5,000,000 g/mol, would be assigned an approximate molecular weight of 5,000,000 g/mol. Likewise, a polyethylene oxide (either a single grade or a blend of grades) meeting the rheological test criteria for both an approximate molecular weight of 900,000 g/mol and of 1,000,000 g/mol (under the respective test conditions as specified above), would be assigned the higher approximate molecular weight of 1,000,000 g/mol.

Similarly, the situation may arise that the viscosity measured for a polyethylene oxide (either a single grade or a blend of grades) using the above rheological test conditions, falls within an herein "undefined" viscosity range, which is herein not assigned to a specific approximate molecular weight. For example, a polyethylene oxide might show a viscosity, which exceeds the viscosity range herein assigned to an approximate molecular weight of 1,000,000 g/mol (under the respective test conditions as specified above), and which, on the other hand, lies below the viscosity range herein assigned to an approximate molecular weight of 2,000,000 g/mol (under the respective test conditions as specified above). For purposes of the invention, such a polyethylene oxide would be assigned the approximate molecular weight which is associated with the viscosity range closest to the measured viscosity.

The term "direct compression" is defined for purposes of the invention as referring to a tableting process, wherein a tablet or any other compressed shaped solid form (such as, the core and/or the shell of a core-shell structure as described herein) is made by a process comprising the steps of dry blending the compounds, e.g., by using a diffusion blend and/or convection mixing process (e.g. Guidance for Industry, SUPAC-IR/MR: Immediate Release and Modified Release Solid Oral Dosage Forms, Manufacturing Equipment Addendum), and compressing the dry blend to obtain the shaped solid form.

For purposes of the invention, the term "active agent" is defined as a pharmaceutically active substance. In certain embodiments, the active agents that can be used here include opioid agonists, opioid antagonists, and/or opioid analgesics. In separate embodiments, the active agents that can be used here include, without limitations, antihistamines (e.g., dimenhydrinate, diphenhydramine, chlorpheniramine and dexchlorpheniramine maleate); non-steroidal anti-inflammatory agents (e.g., naproxen, diclofenac, indomethacin, ibuprofen, sulindac, Cox-2 inhibitors) and acetaminophen; anti-cancer agents (e.g., tamoxifen, gefitinib, letrozole, anastrozole, bicalutamide, flutamide, imatinib, temozolomide, etoposide, paclitaxel, and etc.); antidepressants (e.g., citalopram, escitalopram, paroxetine, fluoxetine, fluvoxamine, sertraline, and etc.); anti-emetics (e.g., metoclopramide, meth-5-ylnaltrexone); anti-epileptics (e.g., phenyloin, meprobmate and nitrazepam); vasodilators (e.g., nifedipine, papaverine, diltiazem and nicardipine); anti-tussive agents and expectorants (e.g., codeine phosphate); anti-asthmatics (e.g., theophylline); antacids; anti-spasmodics (e.g., atropine, scopolamine); antidiabetics (e.g., insulin); diuretics (e.g., ethacrynic acid, bendrofluthiazide); anti-hypotensives (e.g., propranolol, clonidine); antihypertensives (e.g., clonidine, methyldopa); bronchodilabors (e.g., albuterol); steroids (e.g., hydrocortisone, triamcinolone, prednisone); antibiotics (e.g., tetracycline); antihemorrhoidals; hypnotics; psychotropics; antidiarrheals; mucolytics; sedatives; decongestants (e.g., pseudoephedrine); laxatives; vitamins; stimulants, including CNS-stimulants (e.g., methylphenidate, amphetamine, dextroamphetamine, and mazindol); non-opioid analgesics (e.g., acetaminophen); appetite suppressants (e.g., phenylpropanolamine); and cannabinoids.

It is understood that the active agents can be used in either a free base form (or free acid form) or a pharmaceutically acceptable salt form. The free base (or free acid) of the active agent and the pharmaceutically acceptable salts of the active agent may be present in solvent free form, such as in anhydrous form, in solvated form, such as in hydrated form, and as complex, and as mixtures of the foregoing. Further, the active agents can be isotopically-labeled (i.e., radio-labeled). Examples of isotopes that can be used in accordance with the invention include isotopes of hydrogen, carbon, nitrogen, oxygen, phosphorous, fluorine and chlorine, such as $^{2}H$, $^{3}H$, $^{11}C$, $^{13}C$, $^{14}N$, $^{15}N$, $^{18}O$, $^{17}O$, $^{31}P$, $^{32}P$, $^{35}S$, $^{18}F$ and $^{36}Cl$, respectively, and preferably $^{3}H$, $^{11}C$, and $^{14}C$.

For purposes of the invention, the active agent (A) differs from the active agent (B). This means that active agent (A) and active agent (B) differ in the structure of the active agent molecule. Two salt forms of the same active agent molecule (e.g., morphine hydrochloride vs. morphine sulfate) are not regarded as different.

For purposes of the invention, the term "opioid agonist (s)" means one or more compounds selected from the group consisting of pure opioid agonists, mixed opioid agonist-antagonists, partial opioid agonists, and mixtures thereof. The term "opioid agonist" encompasses the free base form of the opioid agonist and pharmaceutically acceptable salts thereof. The free base and the pharmaceutically acceptable salts of the opioid agonist may be present in solvent free form, such as in anhydrous form, in solvated form, such as in hydrated form, and as complex, and as mixtures of the foregoing.

For purposes of this invention, the term "opioid analgesic" means one or more compounds having an analgesic effect, which are selected from the group consisting of pure opioid agonists, mixed opioid agonist-antagonists, partial opioid agonists, and mixtures thereof. The term "opioid analgesic" encompasses the free base form of the opioid analgesic and pharmaceutically acceptable salts thereof. The free base and the pharmaceutically acceptable salts of the opioid analgesic may be present in solvent free form, such as in anhydrous form, in solvated form, such as in hydrated form, and as complex, and as mixtures of the foregoing.

For purposes of the invention, the term "opioid antagonist" encompasses the free base form of the opioid antagonist and pharmaceutically acceptable salts thereof. The free base and the pharmaceutically acceptable salts of the opioid antagonist may be present in solvent free form, such as in anhydrous form, in solvated form, such as in hydrated form, and as complex, and as mixtures of the foregoing.

The term "opioid-induced adverse pharmacodynamic response" means an unintendedside effect experienced by a patient receiving opioid therapy for an intended therapeutic effect. Typically, the intended effect is analgesia and the opioid an opioid analgesic. Unintended side effects associated with opioid therapy include euphoria, feeling high, bowel dysfunction, nausea, vomiting, somnolence, dizziness, respiratory depression, lethality, headache, dry mouth, sedation, sweats, asthenia, hypotension, dysphoria, delirium, miosis, pruritis, urticaria, urinary retention, hyperalgesia, allodynia, physical dependence and tolerance, in particular euphoria, feeling high, bowel dysfunction, respiratory depression, and lethality.

For purposes of the invention, the term "salt" includes inorganic acid salts, such as hydrochloride, hydrobromide, sulfate, phosphate and the like; and organic acid salts, such as myristate, formate, acetate, trifluoroacetate, maleate, tartrate, bitartrate and the like; sulfonates, such as, methanesulfonate, benzenesulfonate, p-toluenesulfonate and the like; and amino acid salts such as arginate, asparaginate, glutamate and the like. The salts may be present in solvent free form, such as in anhydrous form, in solvated form, such as in hydrated form, and as complex, and as mixtures of the foregoing. In particular, the salts may be present in solvent free form, such as in anhydrous form, and in solvated form, such as in hydrated form.

For purposes of the invention, the term "oxycodone", unless specifically designated, means either oxycodone base or a pharmaceutically acceptable salt thereof or a mixture thereof. The oxycodone base and pharmaceutically acceptable salts thereof may be present in solvent free form, such as in anhydrous form, in solvated form (such as hydrated form), and as complex, and as mixtures of the foregoing. The same meaning applies mutatis mutandis for other specifically mentioned active agents, such as "buprenorphine", "codeine", "hydrocodone", "hydromorphone", "methadone", "morphine", "oxymorphone", "tramadol", "naloxone", "naltrexone", "methylnaltrexone", and "nalmephene", etc.

In certain embodiments, the term "buprenorphine" also encompasses buprenorphine prodrugs.

For purposes of the invention, the term of "pharmaceutically acceptable salts of the active agent(s)" (e.g., "oxycodone hydrochloride" and "buprenorphine hydrochloride") encompass the solvent free form (such as, the anhydrous form), solvated forms (such as, hydrated forms), and complexes, and mixtures of the foregoing. In particular, the cited terms encompass the solvent-free (anhydrous) salt and/or hydrated salts.

For purposes of the invention, whenever the molecular weight is added in parentheses when a specific form of the active agent with such a molecular weight is referred to. For example, in the situation when (Mw=351.82 g/mol) is added after oxycodone hydrochloride, it refers to the oxycodone hydrochloride that is free of solvents or complexing agents. Likewise, the molecular weight of Mw=467.64 g/mol is added in parentheses after buprenorphine, it refers to the buprenorphine in the free base form that is free of solvents or complexing agents.

PCT International Publication WO 2005/097801 A1 describes a process for lowering the amount of 14-hydroxycodeinone present as impurity in oxycodone hydrochloride to less than 100 ppm. In particular, a process is described wherein an oxycodone hydrochloride having a 14-hydroxycodeinone level of greater than 100 ppm is hydrogenated, thus achieving a level of less than about 25 ppm 14-hydroxycodeinone. Oxycodone hydrochloride having a 14-hydroxycodeinone level of, for example, less than about 25 ppm, less than about 10 ppm, or less than about 5 ppm, is also described in said application. The term "ppm" as used in said application in connection with the 14-hydroxycodeinone content in oxycodone hydrochloride is defined in said application, and in particular in Example 6 thereof. The disclosure of this PCT application is hereby incorporated by reference in its entirety, and in particular with regard to the process, the oxycodone hydrochloride, and the definition for "ppm".

U.S. Pat. No. 9,073,933 claims an oxycodone hydrochloride composition which comprises at least 95% oxycodone hydrochloride, 8a,14-dihydroxy-7,8-dihydrocodeinone, and less than 25 ppm of 14-hydroxycodeinone, and in one embodiment also less than 5 ppm codeinone. U.S. Pat. No. 7,683,072 claims an oxycodone hydrochloride active pharmaceutical ingredient having less than 25 ppm 14-hydroxycodeinone, wherein at least a portion of the 14-hydroxycodeinone is derived from 8a,14-dihydroxy-7,8-dihydrocodeinone. U.S. Pat. No. 9,522,919 claims an oxycodone hydrochloride composition comprising oxycodone hydrochloride and 8a,14-dihydroxy-7,8-dihydrocodeinone, wherein the ratio of 8a,14-dihydroxy-7,8-dihydrocodeinone to oxycodone HCl is 0.04% or less as measured by HPLC. And in one embodiment, said oxycodone hydrochloride composition further comprises less than 100 ppm 14-hydroxycodeinone. The term "ppm" as used in said patents in connection with the 14-hydroxycodeinone content in oxycodone hydrochloride is defined in said patents, and in particular in Example 6 thereof. The disclosure of each of these patents is hereby incorporated by reference in its entirety, and in particular with regard to the oxycodone hydrochloride composition and the definition for "ppm".

In certain embodiments of the invention wherein the active agent is oxycodone hydrochloride, oxycodone hydrochloride can be used having a 14-hydroxycodeinone level of less than about 100 ppm, less than about 25 ppm, less than about 15 ppm, less than about 10 ppm, less than about 5 ppm, less than about 2 ppm, less than about 1 ppm, less than about 0.5 ppm, or less than about 0.25 ppm, "ppm" being defined as described in WO 2005/097801, and in particular Example 6 thereof. In certain embodiments, oxycodone hydrochloride is used having a 14-hydroxycodeinone level of less than about 25 ppm or less than about 10 ppm. In certain embodiments, said oxycodone hydrochloride is prepared using a process for lowering the amount of 14-hydroxycodeinone present as impurity in oxycodone hydrochloride as described in WO 2005/097801.

The term "pain" means moderate to severe, acute, and/or chronic pain of malignant and non-malignant origin, in particular, severe to most severe, acute and chronic pain of malignant and non-malignant origin, including but not limited to, nociceptive pain, neuropathic pain, and visceral pain. Examples include, but are not limited to, severe pain resulting from diseases such as cancer, rheumatism and arthritis. Further examples are post-operative pain, cluster headaches, dental pain, surgical pain, pain resulting from severe burns, pain from third degree burns, back pain, lower back pain, herpes neuralgia, phantom limb pain, central pain, bone injury pain, and pain during labor and delivery.

The term "patient" means a subject, such as a mammal, particularly a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are entirely normal in all respects or with respect to a particular condition.

DETAILED DESCRIPTION

Figure 1:
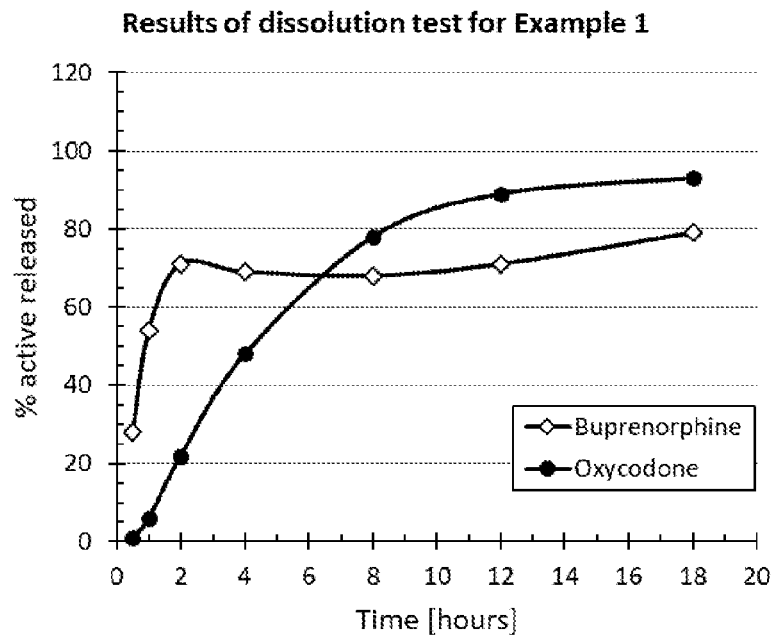
FIG. 1 is a graph depicting the results of the in vitro dissolution test of tablets according to Example 1.

In certain embodiments, the invention is directed to a solid oral extended release dosage form comprising a core-shell structure comprising an active agent (A) and an active agent (B), wherein the core-shell structure comprises (1) a core comprising a first matrix formulation, the first matrix formulation comprising at least one active agent selected from active agent (A) and active agent (B); and (2) a shell encasing the core and consisting of a second matrix formulation, wherein the weight ratio of the first matrix formulation to the second matrix formulation is from about 1:10 to about 4:1.

In certain embodiments, the weight ratio of the first matrix formulation to the second matrix formulation is from about 1:10 to about 3:1, or from about 1:8 to about 3:1. In certain embodiments, the weight ratio of the first matrix formulation to the second matrix formulation is from about 1:7 to about 3:1, from about 1:6 to about 3:1, or from about 1:5 to about 3:1. In certain embodiments, the weight ratio of the first matrix formulation to the second matrix formulation is from about 1:5 to about 2:1, from about 1:5 to about 1:1, from about 1:5 to about 9:10, from about 1:4 to about 9:10, or from about 1:4 to about 5:6.

In certain embodiments, the dosage form comprises a total amount of active agent (A) and a total amount of active agent (B), wherein at least 90 weight % of the total amount of active agent (A) and at least 90 weight % of the total amount of active agent (B) are contained in the first matrix formulation and/or the second matrix formulation of the core-shell structure. In certain embodiments, at least 95 weight % of the total amount of active agent (A) and at least 95 weight % of the total amount of active agent (B) are contained in the first matrix formulation and/or the second matrix formulation of the core-shell structure. In certain embodiments, the total amount of active agent (A) and the total amount of active agent (B) are contained in the first matrix formulation and/or the second matrix formulation of the core-shell structure. It is understood that the total amount of active agent (A) and the total amount of active agent (B) contained in the solid oral extended release dosage form each represent a therapeutically effective amount.

In certain embodiments, the core comprises from about 90 weight-% to about 100 weight-%, or from about 95 weight-% to about 100 weight-%, or from about 98 weight-% to about 100 weight-% of the first matrix formulation. The indicated weight percentage values are based on the weight of the core. In certain embodiments, the core consists of the first matrix formulation.

Matrix Formulations

In certain embodiments, the first matrix formulation comprises at least one material selected from the group consisting of polyethylene oxides, acrylic polymers, alkylcelluloses, cellulose ethers, waxes, shellacs, gums, acrylic resins, polyacrylates, polymethacrylates, copolymers, and mixtures thereof.

In certain embodiments, the first matrix formulation comprises at least one material selected from the group consisting of polyethylene oxides having, based on rheological measurements, an approximate molecular weight of from 100,000 g/mol to 900,000 g/mol, polyethylene oxides having, based on rheological measurements, an approximate molecular weight of from 1,000,000 g/mol to 8,000,000 g/mol, acrylic and methacrylic acid polymers and copolymers, ethylcellulose, hydroxyalkylcelluloses, hydroxypropylmethylcellulose, carboxyalkyl-celluloses, carboxymethylcelluloses, waxes selected from natural and synthetic waxes, fatty acids, and fatty alcohols, hydrogenated castor oil, hydrogenated vegetable oil, and mixtures thereof.

In certain embodiments, the first matrix formulation comprises from about 20 weight-% to about 99 weight-%, or from about 40 weight-% to about 99 weight-%, or from about 50 weight-% to about 99 weight-%, or from about 60 weight-% to about 99 weight-% of said at least one material. In certain embodiments, the first matrix formulation comprises from about 20 weight-% to about 98 weight-%, or from about 40 weight-% to about 98 weight-%, or from about 50 weight-% to about 95 weight-%, or from about 60 weight-% to about 95 weight-% of said at least one material. The indicated weight percentage values are based on the weight of the first matrix formulation.

In certain embodiments, the second matrix formulation comprises at least one material selected from the group consisting of polyethylene oxides, alkylcelluloses, cellulose ethers, waxes, shellacs, gums, acrylic resins, polyacrylates, polymethacrylates, and mixtures thereof. In certain embodiments, the second matrix formulation comprises at least one material selected from the group consisting of polyethylene oxides having, based on rheological measurements, an approximate molecular weight of from 100,000 g/mol to 900,000 g/mol, polyethylene oxides having, based on rheological measurements, an approximate molecular weight of from 1,000,000 g/mol to 8,000,000 g/mol, acrylic and methacrylic acid polymers and copolymers, ethylcellulose, hydroxyalkylcelluloses, hydroxypropylmethylcellulose, carboxyalkylcelluloses, carboxymethylcelluloses, waxes selected from natural and synthetic waxes, fatty acids, and fatty alcohols, hydrogenated castor oil, hydrogenated vegetable oil, and mixtures thereof.

In certain embodiments, the second matrix formulation comprises from about 20 weight-% to about 100 weight-%, or from about 40 weight-% to about 100 weight-%, or from about 50 weight-% to about 100 weight-%, or from about 60 weight-% to about 100 weight-%, or from about 80 weight-% to about 100 weight-% of said at least one material. In certain embodiments, the second matrix formulation comprises from about 20 weight-% to about 99 weight-%, or from about 40 weight-% to about 99 weight-%, or from about 50 weight-% to about 99 weight-%, or from about 60 weight-% to about 99 weight-%, or from about 80 weight-% to about 99 weight-% of said at least one material. In certain embodiments, the second matrix formulation comprises from about 40 weight-% to about 98 weight-%, or from about 50 weight-% to about 98 weight-%, or from about 60 weight-% to about 98 weight-%, or from about 80 weight-% to about 98 weight-%, or from about 80 weight-% to about 98 weight-% of said at least one material. The indicated weight percentage values are based on the weight of the second matrix formulation.

In certain embodiments, the first matrix formulation further comprises a lubricant. In certain embodiments, the first matrix formulation comprises from about 0.5 weight-% to about 30 weight-%, or from about 0.5 weight-% to about 2 weight-% of the lubricant. The indicated weight percentage values are based on the weight of the first matrix formulation.

In certain embodiments, the second matrix formulation further comprises a lubricant. In certain embodiments, the second matrix formulation comprises from about 0.5 weight-% to about 5 weight-%, or from about 0.5 weight-% to about 2 weight-% of the lubricant. The indicated weight percentage values are based on the weight of the second matrix formulation.

In certain embodiments, both the first matrix formulation and the second matrix formulation comprise a lubricant. In certain embodiments, both the first matrix formulation and the second matrix formulation comprise from about 0.5 weight-% to about 2 weight-% of the lubricant.

In certain embodiments, the lubricant included in the first matrix formulation and/or the second matrix formulation is selected from the group consisting of magnesium stearate, calcium stearate, glyceryl monostearate, glyceryl behenate, glyceryl palmitostearate, magnesium lauryl sulfate, sodium lauryl sulfate, sodium stearyl fumarate, zinc stearate, stearic acid, and mixtures thereof. In certain embodiments, the lubricant included in the first matrix formulation and/or the second matrix formulation is magnesium stearate.

Matrix Formulations Comprising Polyethylene Oxide

In certain embodiments, the first matrix formulation comprises at least one polyethylene oxide.

In certain embodiments, the first matrix formulation comprises at least one polyethylene oxide having, based on rheological measurements, an approximate molecular weight of from 100,000 g/mol to 900,000 g/mol, or of from 100,000 g/mol to 600,000 g/mol, or of from 100,000 g/mol to 300,000 g/mol. In certain embodiments, the first matrix formulation comprises at least one polyethylene oxide having, based on rheological measurements, an approximate molecular weight of 100,000 g/mol, 200,000 g/mol, 300,000 g/mol, 600,000 g/mol or 900,000 g/mol.

In certain embodiments, the first matrix formulation comprises at least one polyethylene oxide having, based on rheological measurements, an approximate molecular weight of from 1,000,000 g/mol to 8,000,000 g/mol, or of from 2,000,000 g/mol to 8,000,000 g/mol, or of from 4,000,000 g/mol to 8,000,000 g/mol. In certain embodiments, the first matrix formulation comprises at least one polyethylene oxide having, based on rheological measurements, an approximate molecular weight of 4,000,000 g/mol, 5,000,000 g/mol, 7,000,000 g/mol, or 8,000,000 g/mol. In certain embodiments, the first matrix formulation comprises at least one polyethylene oxide having, based on rheological measurements, an approximate molecular weight of 4,000,000 g/mol, or 5,000,000 g/mol. In certain embodiments, the first matrix formulation comprises at least one polyethylene oxide having, based on rheological measurements, an approximate molecular weight of 4,000,000 g/mol.

For example, the following polyethylene oxide grades are commercially available from Dow Chemical company under the tradename POLYOX® Water-Soluble Resins NF, and can be used in embodiments of the invention:

| PEO grade | Approximate molecular weight (based on rheological measurements) |
|---|---|
| POLYOX ® WSR N-10 NF | 100,000 |
| POLYOX ® WSR N-80 NF | 200,000 |
| POLYOX ® WSR N-750 NF | 300,000 |
| POLYOX ® WSR-205 NF | 600,000 |
| POLYOX ® WSR-1105 NF | 900,000 |
| POLYOX ® WSR N-12K NF | 1,000,000 |
| POLYOX ® WSR N-60K NF | 2,000,000 |
| POLYOX ® WSR-301 NF | 4,000,000 |
| POLYOX ® WSR Coagulant NF | 5,000,000 |
| POLYOX ® WSR-303 NF | 7,000,000 |

In certain embodiments, the first matrix formulation comprises from about 20 weight-% to about 99 weight-%, or from about 40 weight-% to about 99 weight-%, or from about 50 weight-% to about 99 weight-%, or from about 60 weight-% to about 99 weight-% of said at least one polyethylene oxide. In certain embodiments, the first matrix formulation comprises from about 20 weight-% to about 98 weight-%, or from about 40 weight-% to about 98 weight-%, or from about 50 weight-% to about 95 weight-%, or from about 60 weight-% to about 95 weight-% of said at least one polyethylene oxide. The indicated weight percentage values are based on the weight of the first matrix formulation.

In certain embodiments, in the first matrix formulation, the at least one polyethylene oxide, the optional active agent (A), the optional active agent (B), and an optional lubricant together make up from about 95 weight-% to about 100 weight-% of the first matrix formulation, or from about 98 weight-% to about 100 weight-% of the first matrix formulation, or from about 99 weight-% to about 100 weight-% of the first matrix formulation. The indicated weight percentage values are based on the weight of the first matrix formulation.

In certain embodiments, the second matrix formulation comprises at least one polyethylene oxide.

In certain embodiments, the second matrix formulation comprises at least one polyethylene oxide having, based on rheological measurements, an approximate molecular weight of from 100,000 g/mol to 900,000 g/mol, or of from 100,000 g/mol to 600,000 g/mol, or of from 100,000 g/mol to 300,000 g/mol. In certain embodiments, the second matrix formulation comprises at least one polyethylene oxide having, based on rheological measurements, an approximate molecular weight of 100,000 g/mol, 200,000 g/mol, 300,000 g/mol, 600,000 g/mol or 900,000 g/mol. In certain embodiments, the second matrix formulation comprises at least one polyethylene oxide having, based on rheological measurements, an approximate molecular weight of 100,000 g/mol, 200,000 g/mol, or 300,000 g/mol. In certain embodiments, the second matrix formulation comprises at least one polyethylene oxide having, based on rheological measurements, an approximate molecular weight of 100,000 g/mol.

In certain embodiments, the second matrix formulation comprises at least one polyethylene oxide having, based on rheological measurements, an approximate molecular weight of from 1,000,000 g/mol to 8,000,000 g/mol, or of from 2,000,000 g/mol to 8,000,000 g/mol, or of from 4,000,000 g/mol to 8,000,000 g/mol. In certain embodiments, the second matrix formulation comprises at least one polyethylene oxide having, based on rheological measurements, an approximate molecular weight of 4,000,000 g/mol, 5,000,000 g/mol, 7,000,000 g/mol, or 8,000,000 g/mol.

In certain embodiments, the second matrix formulation comprises from about 20 weight-% to about 100 weight-%, or from about 40 weight-% to about 100 weight-%, or from about 50 weight-% to about 100 weight-%, or from about 60 weight-% to about 100 weight-%, or from about 80 weight-% to about 100 weight-% of said at least one polyethylene oxide. In certain embodiments, the second matrix formulation comprises from about 20 weight-% to about 99 weight-%, or from about 40 weight-% to about 99 weight-%, or from about 50 weight-% to about 99 weight-%, or from about 60 weight-% to about 99 weight-%, or from about 80 weight-% to about 99 weight-% of said at least one polyethylene oxide. In certain embodiments, the second matrix formulation comprises from about 40 weight-% to about 98 30 weight-%, or from about 50 weight-% to about 98 weight-%, or from about 60 weight-% to about 98 weight-%, or from about 80 weight-% to about 98 weight-%, or from about 85 weight-% to about 98 weight-% of said at least one polyethylene oxide. The indicated weight percentage values are based on the weight of the second matrix formulation.

In certain embodiments, in the second matrix formulation, the at least one polyethylene oxide, the optional active agent (A), the optional active agent (B), and an optional lubricant together make up from about 95 weight-% to about 100 weight-% of the second matrix formulation, or from about 98 weight-% to about 100 weight-% of the second matrix formulation, or from about 99 weight-% to about 100 weight-% of the second matrix formulation.

In certain embodiments, both the first matrix formulation and the second matrix formulation comprise at least one polyethylene oxide.

In certain embodiments, the first matrix formulation comprises at least one polyethylene oxide having, based on rheological measurements, an approximate molecular weight of from 100,000 g/mol to 600,000 g/mol, and the second matrix formulation comprises at least one polyethylene oxide having, based on rheological measurements, an approximate molecular weight of from 1,000,000 g/mol to 8,000,000 g/mol.

In certain embodiments, the first matrix formulation comprises at least one polyethylene oxide having, based on rheological measurements, an approximate molecular weight of from 1,000,000 g/mol to 8,000,000 g/mol; and the second matrix formulation comprises at least one polyethylene oxide having, based on rheological measurements, an approximate molecular weight of from 100,000 g/mol to 600,000 g/mol.

In certain embodiments, the first matrix formulation comprises at least one polyethylene oxide having, based on rheological measurements, an approximate molecular weight of from 1,000,000 g/mol to 8,000,000 g/mol; and the second matrix formulation comprises at least one polyethylene oxide having, based on rheological measurements, an approximate molecular weight of from 1,000,000 g/mol to 8,000,000 g/mol.

In certain embodiments, the first matrix formulation comprises from about 50 weight-% to about 95 weight-%, or from about 60 weight-% to about 95 weight-% of said at least one polyethylene oxide (based on the weight of the first matrix formulation), and the second matrix formulation comprises from about 60 weight-% to about 99 weight-%, or from about 80 weight-% to about 98 weight-% of said at least one polyethylene oxide (based on the weight of the second matrix formulation).

In certain embodiments, the first matrix formulation comprises from about 50 weight-% to about 95 weight-%, or from about 60 weight-% to about 95 weight-% (based on the weight of the first matrix formulation) of at least one polyethylene oxide having, based on rheological measurements, an approximate molecular weight of from 2,000,000 g/mol to 8,000,000 g/mol, and the second matrix formulation comprises from about 60 weight-% to about 99 weight-%, or from about 85 weight-% to about 98 weight-% (based on the weight of the second matrix formulation) of at least one polyethylene oxide having, based on rheological measurements, an approximate molecular weight of from 100,000 g/mol to 300,000 g/mol.

In certain embodiments, the first matrix formulation and the second matrix formulation comprise different percentages (weight-%) of polyethylene oxide, different percentages (weight-%) of active agent (A), and/or different percentages (weight-%) of active agent (B).

In certain embodiments, wherein the first matrix formulation comprises at least one polyethylene oxide, the first matrix formulation may be cured by subjecting the first matrix formulation to a temperature of from about 60° C. to about 90° C., or from about 62° C. to about 90° C., for a time period of from about 1 minute to about 24 hours, or from about 5 minutes to about 12 hours, or from about 15 minutes to about 5 hours. In certain embodiments, the curing step is conducted at atmospheric pressure.

In certain embodiments, wherein the first matrix formulation and the second matrix formulation comprise at least one polyethylene oxide, the first matrix formulation and the second matrix formulation may be cured by subjecting the first matrix formulation and the second matrix formulation to a temperature of from about 60° C. to about 90° C., or from about 62° C. to about 90° C., for a time period of from about 1 minute to about 24 hours, or from about 5 minutes to about 12 hours, or from about 15 minutes to about 5 hours. In certain embodiments, the curing step is conducted at atmospheric pressure.

In certain embodiments, the solid oral extended release dosage form as described herein is obtainable by a process comprising the following steps:
  a) combining at least
    at least one polyethylene oxide,
    at least one active agent selected from active agent (A) and active agent (B), and
    optionally a lubricant,
  to form a first composition,
  b) combining at least
    at least one polyethylene oxide, optionally at least one active agent selected from active agent (A) and active agent (B), and optionally a lubricant
to form a second composition,
c) shaping the first composition of step (a) to form the first matrix formulation,
d) optionally curing said first matrix formulation comprising subjecting said first matrix formulation to a temperature of from about 60° C. to about 90° C., or from about 62° C. to about 90° C., for a time period of from about 1 minute to about 24 hours,
e) applying the second composition of step (b) around the first matrix formulation of step (c) or (d) to form the second matrix formulation encasing the first matrix formulation;
f) optionally curing said first matrix formulation and said second matrix formulation comprising subjecting said first matrix formulation and said second matrix formulation to a temperature of from about 60° C. to about 90° C., or from about 62° C. to about 90° C., for a time period of from about 1 minute to about 24 hours.

In certain embodiments, the first composition is shaped in step (c) by direct compression of said first composition. In certain embodiments, the second composition is applied in step (e) by compression-coating said second composition. In certain embodiments, the optional curing step (d) and/or (f) is conducted at atmospheric pressure.

The curing process may provide the matrix formulation(s) with a certain hardness, which can impede the crushing or pulverization of the dosage form.

Solid Oral Extended Release Dosage Form

In certain embodiments, the solid oral extended release dosage form as described herein is in the form of a tablet or a capsule. In certain embodiments, the solid oral extended release dosage form as described herein is in the form of a tablet. In certain embodiments, the solid oral extended release dosage form as described herein is in the form of a capsule.

In other embodiments, the solid oral extended release dosage forms of the invention comprise other extended release formulations known in the art. For example, the core-shell structure of the invention may be present in the form of coated beads, coated pellets, coated tablets or ion exchange resins.

In certain embodiments, the solid oral extended release dosage form as described herein comprises a plurality of particles, wherein each particle comprises said core-shell structure.

In certain embodiments, the solid oral extended release dosage form as described herein comprises at least two minitablets, each minitablet comprising said core-shell structure.

In certain embodiments, the core-shell structure contained in the dosage form is in the form of a single-unit dose tablet. In certain embodiments, the core is a compressed tablet and the shell is a compression coating.

In certain embodiments, the core and the shell are visually indistinguishable. In certain embodiments, the first matrix formulation (of the core) and the second matrix formulation (of the shell) have a Commission international de l'eclairage (CIE) L*A*B* value within 10% of each other.

Active Agents

In certain embodiments, the molar ratio of the active agent (A) contained in the dosage form to the active agent (B) contained in the dosage form is from about 1:100 to about 100:1, or from about 1:50 to about 50:1, or from about 1:30 to about 30:1, or from about 1:1 to about 30:1, or from about 1:1 to about 20:1.

The active agent that can be used in accordance with the invention can be any pharmaceutically active substance, either in the free base form or the pharmaceutically acceptable salt form. In certain embodiments, the active agent (A) and the active agent (B) belong to the same class of compounds (e.g., opioid analgesics). In other embodiments, the active agent (A) and the active agent (B) belong to different classes of compounds; for example, one active agent is an anti-epileptic drug, and the other active agent is a non-opioid analgesic.

In certain embodiments, the active agent (A) is an opioid agonist, and the active agent (B) is selected from the group consisting of antihistamines, non-steroidal anti-inflammatory agents, anti-emetics, anti-cancer agents, antidepressant agents, anti-epileptics, vasodilators, anti-tussive agents and expectorants, anti-asthmatics, antacids, anti-spasmodics, antidiabetics, diuretics, anti-hypotensives, antihypertensives, bronchodilators, steroids, antibiotics, antihemorrhoidals, hypnotics, psychotropics, antidiarrheals, mucolytics, sedatives, decongestants, laxatives, vitamins, stimulants, appetite suppressants, non-opioid analgesics, 30 and cannabinoids.

In certain embodiments, the active agent (A) is an opioid agonist, and the active agent (B) is a non-opioid analgesic. In certain embodiments, the non-opioid analgesic is selected from the group consisting of non-steroidal anti-inflammatory agents. In certain embodiments, the non-opioid analgesic is acetaminophen.

In certain embodiments, the active agent (A) is an opioid agonist, and the active agent (B) is an opioid antagonist. In certain embodiments, the opioid antagonist is selected from the group consisting of naloxone, naltrexone, methylnaltrexone, and nalmephene.

In certain embodiments, the active agent (A) is an opioid agonist, and the active agent (B) is a different opioid agonist.

In certain embodiments, the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, and tramadol. In certain embodiments, the opioid agonist is selected from the group consisting of codeine, hydrocodone, hydromorphone, methadone, morphine, oxycodone, oxymorphone, and tramadol.

In certain embodiments, the active agent (A) is selected from the group consisting of codeine, hydrocodone, hydromorphone, methadone, morphine, oxycodone, oxymorphone, and tramadol, and the active agent (B) is buprenorphine. In certain embodiments, the active agent (A) is oxycodone, and the active agent (B) is buprenorphine.

In certain embodiments comprising buprenophine as the active agent (B), the dosage form can comprise a total amount of buprenorphine which is equimolar to from about 0.5 mg to about 20 mg, or from about 2 mg to about 20 mg, or from about 2 mg to about 16 mg, of buprenorphine base (Mw=467.64 g/mol). In certain embodiments, the active agent (B) is buprenorphine hydrochloride and the dosage form comprises a total amount of buprenorphine hydrochloride which is equimolar to from about 0.5 mg to about 20 mg, or from about 2 mg to about 20 mg, or from about 2 mg to about 16 mg, of buprenorphine base (Mw=467.64 g/mol).

In certain embodiments comprising oxycodone as the active agent (A), the dosage form can comprise a total amount of oxycodone which is equimolar to from about 5 mg to about 500 mg, or from about 5 mg to about 160 mg, or from about 5 mg to about 120 mg, or from about 10 mg to about 80 mg of oxycodone hydrochloride (Mw=351.82 g/mol). In certain embodiments, the active agent (A) is oxycodone hydrochloride and the dosage form comprises a total amount of oxycodone hydrochloride which is equimolar to from about 5 mg to about 500 mg, or from about 5 mg to about 160 mg, or from about 5 mg to about 120 mg, or from about 10 mg to about 80 mg, of oxycodone hydrochloride (Mw=351.82 g/mol). In certain embodiments, the dosage form comprises a total amount of oxycodone hydrochloride which is equimolar to about 5 mg, about 7.5 mg, about 10 mg, about 15 mg, about 20 mg, about 30 mg, about 40 mg, about 45 mg, about 60 mg, about 80 mg, about 90 mg, about 120 mg or about 160 mg of oxycodone hydrochloride (Mw=351.82 g/mol).

In certain embodiments, the active agent (A) is oxycodone, and the active agent (B) is buprenorphine, and the dosage form comprises a total amount of oxycodone which is equimolar to from about 10 mg to about 80 mg of oxycodone hydrochloride (Mw=351.82 g/mol), and a total amount of buprenorphine which is equimolar to from about 0.5 mg to about 20 mg of buprenorphine base (Mw=467.64 g/mol). In certain embodiments, oxycodone is oxycodone hydrochloride, and buprenorphine is buprenorphine hydrochloride.

In certain embodiments, the active agent (A) is oxycodone, and the active agent (B) is buprenorphine, and the dosage form comprises
a total amount of oxycodone, and
a total amount of buprenorphine,
wherein the weight ratio of the total amount of oxycodone in the dosage form to the total amount of buprenorphine in the dosage form is from about 3:1 to about 20:1, calculated with the total amount of oxycodone in the dosage form expressed as the equimolar amount of oxycodone hydrochloride (Mw=351.82 g/mol) in mg and the total amount of buprenorphine in the dosage form expressed as the equimolar amount of buprenorphine base (Mw=467.64 g/mol) in mg. In certain embodiments, the weight ratio of the total amount of oxycodone in the dosage form to the total amount of buprenorphine in the dosage form is from about 4:1 to about 20:1, or from about 4:1 to about 10:1, or from about 5:1 to about 10:1. In certain embodiments, oxycodone is oxycodone hydrochloride, and buprenorphine is buprenorphine hydrochloride.

Distribution of Active Agents (A) and (B) Between the First and the Second Matrix Formulations In certain embodiments, the invention is directed to a solid oral extended release dosage form comprising a core-shell structure comprising an active agent (A) and an active agent (B), wherein the core-shell structure comprises
(1) a core comprising a first matrix formulation, the first matrix formulation comprising at least one active agent selected from active agent (A) and active agent (B); and
(2) a shell encasing the core and consisting of a second matrix formulation, the second matrix formulation comprising at least one active agent selected from active agent (A) and active agent (B), wherein the weight ratio of the first matrix formulation to the second matrix formulation is from about 1:10 to about 4:1.

In certain embodiments, the first matrix formulation comprises both active agent (A) and active agent (B), and the second matrix formulation comprises at least one active agent selected from active agent (A) and active agent (B). In other embodiments, the first matrix formulation comprises at least one active agent selected from active agent (A) and active agent (B), and the second matrix formulation comprises both active agent (A) and active agent (B).

Thus, in certain embodiments, the core-shell structure comprises
(1) a core comprising a first matrix formulation, the first matrix formulation comprising both active agent (A) and active agent (B); and
(2) a shell encasing the core and consisting of a second matrix formulation, the second matrix formulation comprising at least one active agent selected from active agent (A) and active agent (B).

In other embodiments, the core-shell structure comprises
(1) a core comprising a first matrix formulation, the first matrix formulation comprising at least one active agent selected from active agent (A) and active agent (B); and
(2) a shell encasing the core and consisting of a second matrix formulation, the second matrix formulation comprising both active agent (A) and active agent (B).

In certain embodiments (referred to herein "embodiment #1"), the core-shell structure comprises
(1) a core comprising a first matrix formulation, the first matrix formulation comprising both active agent (A) and active agent (B); and
(2) a shell encasing the core and consisting of a second matrix formulation, the second matrix formulation comprising both active agent (A) and active agent (B).

In certain embodiments (referred to herein "embodiment #2"), the core-shell structure comprises
(1) a core comprising a first matrix formulation, the first matrix formulation comprising both active agent (A) and active agent (B); and
(2) a shell encasing the core and consisting of a second matrix formulation, the second matrix formulation comprising active agent (B) and no active agent (A).

In certain embodiments (referred to herein "embodiment #3"), the core-shell structure comprises
(1) a core comprising a first matrix formulation, the first matrix formulation comprising both active agent (A) and active agent (B); and
(2) a shell encasing the core and consisting of a second matrix formulation, the second matrix formulation comprising active agent (A) and no active agent (B).

In certain embodiments (referred to herein "embodiment #4"), the core-shell structure comprises
(1) a core comprising a first matrix formulation, the first matrix formulation comprising active agent (A) and no active agent (B); and (2) a shell encasing the core and consisting of a second matrix formulation, the second matrix formulation comprising both active agent (A) and active agent (B).

In certain embodiments (referred to herein "embodiment #5"), the core-shell structure comprises (1) a core comprising a first matrix formulation, the first matrix formulation comprising active agent (B) and no active agent (A); and (2) a shell encasing the core and consisting of a second matrix formulation, the second matrix formulation comprising both active agent (A) and active agent (B).

In certain embodiments, wherein both the first matrix formulation and the second matrix formulation comprise the active agent (A), the weight ratio of the active agent (A) in the first matrix formulation to the active agent (A) in the second matrix formulation can be from about 1:50 to about 50:1, or from about 1:20 to about 20:1, or from about 1:10 to about 10:1, or from about 1:2 to about 50:1, or from about 1:2 to about 20:1, or from about 1:2 to about 10:1, or from about 1:1 to about 20:1, or from about 1:1 to about 10:1, or from about 1:1 to about 9:1, or from about 1:1 to about 5:1, or from about 2:1 to about 5:1.

In certain embodiments, wherein both the first matrix formulation and the second matrix formulation comprise the active agent (B), the weight ratio of the active agent (B) in the first matrix formulation to the active agent (B) in the second matrix formulation can be from about 1:50 to about 50:1, or from about 1:20 to about 20:1, or from about 1:10 to about 10:1, or from about 1:50 to about 2:1, or from about 1:20 to about 2:1, or from about 1:10 to about 2:1, or from about 1:20 to about 1:1, or from about 1:10 to about 1:1, or from about 1:9 to about 1:1, or from about 1:5 to about 1:1, or from about 1:5 to about 1:2.

In certain embodiments (referred to herein "embodiment #6"), the core-shell structure comprises 1) a core comprising a first matrix formulation, the first matrix formulation comprising active agent (A) and no active agent (B); and 2) a shell encasing the core and consisting of a second matrix formulation, the second matrix formulation comprising active agent (B) and no active agent (A).

In certain embodiments (referred to herein "embodiment #7"), the core-shell structure comprises 1) a core comprising a first matrix formulation, the first matrix formulation comprising active agent (B) and no active agent (A); and 2) a shell encasing the core and consisting of a second matrix formulation, the second matrix formulation comprising active agent (A) and no active agent (B).

In certain embodiments (referred to herein "embodiment #8"), the core-shell structure comprises 1) a core comprising a first matrix formulation, the first matrix formulation comprising both active agent (A) and active agent (B); and 2) a shell encasing the core and consisting of a second matrix formulation, the second matrix formulation comprising neither active agent (A), nor active agent (B).

In certain embodiments (referred to herein "embodiment #1 A"), the core-shell structure comprises 1) a core comprising a first matrix formulation, the first matrix formulation comprising from about 60 weight-% to about 95 weight-% (based on the weight of the first matrix formulation) of at least one polyethylene oxide having, based on rheological measurements, an approximate molecular weight of from 1,000,000 g/mol to 8,000,000 g/mol, a first amount of active agent (A), and a first amount of active agent (B); and 2) a shell encasing the core and consisting of a second matrix formulation, the second matrix formulation comprising from about 80 weight-% to about 98 weight-% (based on the weight of the second matrix formulation) of at least one polyethylene oxide having, based on rheological measurements, an approximate molecular weight of from 100,000 g/mol to 600,000 g/mol, a second amount of active agent (A), and a second amount of active agent (B);

wherein the weight ratio of the first matrix formulation to the second matrix formulation is from about 1:5 to about 2:1. In certain embodiments, the weight ratio of the first matrix formulation to the second matrix formulation is from about 1:5 to about 1:1, or from about 1:5 to about 9:10, or from about 1:4 to about 9:10, or from about 1:3 to about 9:10, or from about 1:4 to about 5:6, or from about 1:3 to about 5:6, or from about 1:2 to about 5:6, or from about 1:2 to about 3:4.

In certain embodiments, the weight ratio of the first amount of active agent (A) to the second amount of active agent (A) is from about 1:2 to about 10:1, and the weight ratio of the first amount of active agent (B) to the second amount of active agent (B) is from about 1:10 to about 2:1.

In other embodiments, the weight ratio of the first amount of active agent (A) to the second amount of active agent (A) is from about 1:1 to about 10:1, and the weight ratio of the first amount of active agent (B) to the second amount of active agent (B) is from about 1:10 to about 1:1.

In separate embodiments, the weight ratio of the first amount of active agent (A) to the second amount of active agent (A) is from about 1:1 to about 9:1, and weight ratio of the first amount of active agent (B) to the second amount of active agent (B) is from about 1:9 to about 1:1.

In certain embodiments, the weight ratio of the first amount of active agent (A) to the second amount of active agent (A) is from about 1:1 to about 5:1, and the weight ratio of the first amount of active agent (B) to the second amount of active agent (B) is from about 1:5 to about 1:1.

In an example of embodiment #1 A, the active agent (A) is an opioid analgesic selected from the group of oxycodone, hydromorphone, fentanyl, morphine, or pharmaceutically acceptable salts thereof; and the active agent (B) is buprenorphine free base or a pharmaceutically acceptable salt thereof (collectively, as "buprenorphine"). In one embodiment, the active agent (A) is oxycodone free base or a pharmaceutically acceptable salt thereof (collectively, as "oxycodone"). In certain embodiments, the weight ratio of the total amount of the opioid analgesic (e.g., oxycodone) in the dosage form to the total amount of buprenorphine in the dosage form is from about 4:1 to about 20:1, or from about 4:1 to about 10:1. In certain embodiments, the active agent (A) in the dosage form is oxycodone hydrochloride, and the active agent (B) in the dosage form is buprenorphine hydrochloride.

In Vitro Release

In certain embodiments, the active agent (A) is oxycodone, and the amount of oxycodone released from the dosage form, as measured by an in-vitro dissolution in a USP Apparatus 1 (basket) at 100 rpm in 900 ml simulated gastric fluid without enzymes (SGF) at 37.0° C., meets at least one of the following criteria (a) to (d):

a) the amount of oxycodone released from the dosage form at 1 hour is from about 3 weight-% to about 45 weight-%; and/or
b) the amount of oxycodone released from the dosage form at 2 hours is from about 10 weight-% to about 65 weight-%; and/or
c) the amount of oxycodone released from the dosage form at 4 hours is from about 40 weight-% to about 80 weight-%; and/or
d) the amount of oxycodone released from the dosage form at 8 hours is from about 70 weight-% to about 98 weight-%.

In certain embodiments, the active agent (A) is oxycodone, and the amount of oxycodone released from the dosage form, as measured by an in-vitro dissolution in a USP Apparatus 1 (basket) at 100 rpm in 900 ml simulated gastric fluid without enzymes (SGF) at 37.0° C., meets at least one of the following criteria (a) to (d):
a) the amount of oxycodone released from the dosage form at 1 hour is from about 5 weight-% to about 35 weight-%; and/or
b) the amount of oxycodone released from the dosage form at 2 hours is from about from 20 weight-% to about 55 weight-%; and/or
c) the amount of oxycodone released from the dosage form at 4 hours is from about 45 weight-% to about 75 weight-%; and/or
d) the amount of oxycodone released from the dosage form at 8 hours is from about 75 weight-% to about 95 weight-%.

In certain embodiments, the active agent (B) is buprenorphine, and the amount of buprenorphine released from the dosage form, as measured by an in-vitro dissolution in a USP Apparatus 1 (basket) at 100 rpm in 900 ml simulated gastric fluid without enzymes (SGF) at 37.0° C., meets at least one of the following criteria (a) to (d):
a) the amount of buprenorphine released from the dosage form at 1 hour is from about 20 weight-% to about 75 weight-%; and/or
b) the amount of buprenorphine released from the dosage form at 2 hours is from about 40 weight-% to about 100 weight-%; and/or
c) the amount of buprenorphine released from the dosage form at 4 hours is from about 45 weight-% to about 100 weight-%; and/or
d) the amount of buprenorphine released from the dosage form at 8 hours is from about 50 weight-% to about 100 weight-%.

In certain embodiments, the active agent (B) is buprenorphine, and the amount of buprenorphine released from the dosage form, as measured by an in-vitro dissolution in a USP Apparatus 1 (basket) at 100 rpm in 900 ml simulated gastric fluid without enzymes (SGF) at 37.0° C., meets at least one of the following criteria (a) to (d):
a) the amount of buprenorphine released from the dosage form at 1 hour is from about 30 weight-% to about 70 weight-%; and/or
b) the amount of buprenorphine released from the dosage form at 2 hours is from about 50 weight-% to about 90 weight-%; and/or
c) the amount of buprenorphine released from the dosage form at 4 hours is from about 55 weight-% to about 95 weight-%; and/or
d) the amount of buprenorphine released from the dosage form at 8 hours is from about 60 weight-% to about 98 weight-%.

In certain embodiments, the active agent (A) is oxycodone and the active agent (B) is buprenorphine, and the amount of buprenorphine (in weight-% based on 100% buprenorphine) released from the dosage form at 1 hour exceeds the amount of oxycodone (in weight-% based on 100% oxycodone) released from the dosage form at 1 hour by a factor of at least 1.1, as measured by an in-vitro dissolution in a USP Apparatus 1 (basket) at 100 rpm in 900 ml simulated gastric fluid without enzymes (SGF) at 37.0° C. In certain embodiments, said factor is at least 1.2, or at least 1.5.

In certain embodiments, the active agent (A) is oxycodone and the active agent (B) is buprenorphine and the amount of buprenorphine (in weight-% based on 100% buprenorphine) released from the dosage form at 2 hours exceeds the amount of oxycodone (in weight-% based on 100% oxycodone) released from the dosage form at 2 hours by a factor of at least 1.1, as measured by an in-vitro dissolution in a USP Apparatus 1 (basket) at 100 rpm in 900 ml simulated gastric fluid without enzymes (SGF) at 37.0° C. In certain embodiments, said factor is at least 1.2, or at least 1.5.

In certain embodiments, the active agent (A) is oxycodone and the active agent (B) is buprenorphine and the amount of buprenorphine (in weight-% based on 100% buprenorphine) released from the dosage form at 4 hours exceeds the amount of oxycodone (in weight-% based on 100% oxycodone) released from the dosage form at 4 hours by a factor of at least 1.1, as measured by an in-vitro dissolution in a USP Apparatus 1 (basket) at 100 rpm in 900 ml simulated gastric fluid without enzymes (SGF) at 37.0° C. In certain embodiments, said factor is at least 1.2, or at least 1.5.

Manufacture of the Solid Dosage Forms

In certain embodiments, the solid oral extended release dosage form as described herein is manufactured by a process comprising the steps of:
(i) combining at least
at least one material selected from the group consisting of polyethylene oxides, alkylcelluloses, cellulose ethers, waxes, shellacs, gums, acrylic resins, polyacrylates, polymethacrylates, and mixtures thereof,
at least one active agent selected from active agent (A) and active agent (B), and optionally a lubricant, to form a first composition,
(ii) combining at least
at least one material selected from the group consisting of polyethylene oxides, alkylcelluloses, cellulose ethers, waxes, shellacs, gums, acrylic resins, polyacrylates, polymethacrylates, and mixtures thereof,
optionally at least one active agent selected from active agent (A) and active agent (B), and
optionally a lubricant
to form a second composition,
(iii) shaping the first composition of step (i) to form the first matrix formulation,
(iv) applying the second composition of step (ii) around the first matrix formulation to form the second matrix formulation encasing the first matrix formulation.

In certain embodiments, the solid oral extended release dosage form as described herein is manufactured by a process comprising the steps of:
(i) combining at least
at least one material selected from the group consisting of polyethylene oxides having, based on rheological measurements, an approximate molecular weight of from 100,000 g/mol to 900,000 g/mol, polyethylene oxides having, based on rheological measurements, an approximate molecular weight of from 1,000,000 g/mol to 8,000,000 g/mol, acrylic and ethacrylic acid polymers and copolymers, ethylcellulose, hydroxyalkylcelluloses, hydroxypropylmethylcellulose, carboxyalkylcelluloses, carboxymethylcelluloses, waxes selected from natural and synthetic waxes, fatty acids, and fatty alcohols, hydrogenated castor oil, hydrogenated vegetable oil, and mixtures thereof,
at least one active agent selected from active agent (A) and active agent (B), and
optionally a lubricant,
to form a first composition,
(ii) combining at least
at least one material selected from the group consisting of polyethylene oxides having, based on rheological measurements, an approximate molecular weight of from 100,000 g/mol to 900,000 g/mol, polyethylene oxides having, based on rheological measurements, an approximate molecular weight of from 1,000,000 g/mol to 8,000,000 g/mol, acrylic and methacrylic acid polymers and copolymers, ethylcellulose, hydroxyalkylcelluloses, hydroxypropylmethylcellulose, carboxyalkylcelluloses, carboxymethylcelluloses, waxes selected from natural and synthetic waxes, fatty acids, and fatty alcohols, hydrogenated castor oil, hydrogenated vegetable oil, and mixtures thereof,
optionally at least one active agent selected from active agent (A) and active agent (B), and
optionally a lubricant
to form a second composition,
(iii) shaping the first composition of step (i) to form the first matrix formulation,
(iv) applying the second composition of step (ii) around the first matrix formulation to form the second matrix formulation encasing the first matrix formulation.

The shaping step (iii) can be performed, e.g., by direct compression, extrusion or molding of the first composition to form the first matrix formulation. However, any other process known in the mi for manufacturing tablets or tablet cores, may also be used, such as wet granulation and subsequent compression of the granules to form tablets.

In certain embodiments, the first composition is shaped in step (iii) by direct compression of said first composition. Direct compression is an efficient and simple process for shaping tablets by avoiding process steps like wet granulation. Direct compression can be used, e.g., to prepare core-shell structures in the form of tablets or minitablets, wherein the core is a compressed tablet and the shell is a compression coating.

Step (iv) can be performed, e.g. by compression coating, molding, or spraying of the second composition, or by dipping into the second composition. In certain embodiments, the second composition is applied in step (iv) by compression-coating said second composition.

In certain embodiments, the first composition is shaped in step (iii) by direct compression of said first composition, and the second composition is applied in step (iv) by compression-coating said second composition.

In certain embodiments, the processes as described above comprise a further step (v) of coating the core-shell structure (e.g., by coating the second matrix formulation). In certain embodiments, the coating is a film coating (e.g., a cosmetic film coating such as an Opadry® coating).

In certain embodiments, the invention is also directed to a solid oral extended release dosage form as described herein obtainable by the described processes of manufacture.

In certain embodiments, the solid oral extended release dosage form as described herein is manufactured by a process comprising the steps of:
a) combining at least
at least one polyethylene oxide,
at least one active agent selected from active agent (A) and active agent (B), and
optionally a lubricant,
to form a first composition,
b) combining at least
at least one polyethylene oxide,
optionally at least one active agent selected from active agent (A) and active agent (B), and
optionally a lubricant to form a second composition,
c) shaping the first composition of step (a) to form the first matrix formulation,
d) optionally curing said first matrix formulation comprising subjecting said first matrix formulation to a temperature of from about 60° C. to about 90° C., or from about 62° C. 5 to about 90° C., for a time period of from about 1 minute to about 24 hours,
e) applying the second composition of step (b) around the first matrix formulation of step (c) or (d) to form the second matrix formulation encasing the first matrix formulation;
f) optionally curing said first matrix formulation and said second matrix formulation comprising subjecting said first matrix formulation and said second matrix formulation to a temperature of from about 60° C. to about 90° C., or from about 62° C. to about 90° C., for a time period of from about 1 minute to about 24 hours.

The shaping step (c) can be performed, e.g., by direct compression, extrusion or molding of the first composition to form the first matrix formulation (due to the elevated temperature applied during extrusion or molding, a subsequent curing step may be unnecessary). However, any other process known in the art for manufacturing tablets or tablet cores, may also be used, such as wet granulation and subsequent compression of the granules to form tablets.

In certain embodiments, the first composition is shaped in step (c) by direct compression of said first composition. Direct compression can be used, e.g., to prepare core-shell structures in the form of tablets or minitablets, wherein the core is a compressed tablet and the shell is a compression coating.

Step (e) of applying the second composition can be performed, e.g. by compression coating, molding, or spraying of the second composition, or by dipping into the second composition. In certain embodiments, the second composition is applied in step (e) by compression-coating said second composition.

In certain embodiments, the first composition is shaped in step (c) by direct compression of said first composition, and the second composition is applied in step (e) by compression-coating said second composition. In certain such embodiments, the core is a compressed tablet and the shell is a compression coating.

The process of manufacture, and in particular, the shaping step (c) and the optional curing steps (d) and/or (f) including curing temperatures, curing times with starting points and end points of the curing, and devices used for the curing step, can be conducted in analogy to the teaching of PCT publication WO 2008/023261, in particular paragraphs [0046], [00126] to [00146], [00159] to [00161] thereof, the contents of which are hereby incorporated by reference. The shaping step (c) and step (e) of applying the second composition, including techniques and respective devices, as well as the optional curing steps (d) and/or (f) including curing temperatures, curing times with starting points and end points of the curing, and devices used for the curing step, can also be conducted in analogy to the teaching of PCT publication WO 2012/085656, in particular paragraphs [00 113] to [00116], [00126] to [00132] and [00165] to [00187] thereof, the contents of which are hereby incorporated by reference.

In certain embodiments, the curing of step (d) and/or (f) is conducted at atmospheric pressure.

In certain embodiments, the curing of step (d) and/or (f) is conducted by subjecting the extended release matrix formulation to a temperature of from about 60° C. to about 90° C. for a time period of from about 1 minute to about 24 hours.

In certain embodiments, the curing of step (d) and/or (f) is conducted by subjecting the extended release matrix formulation to a temperature of from about 62° C. to about 85° C. for a time period of from about 5 minutes to about 5 hours.

In certain embodiments, the curing of step (d) and/or (f) is conducted by subjecting the extended release matrix formulation to a temperature of from about 65° C. to about 85° C. for a 20 time period of from about 15 minutes to about 2 hours.

In certain embodiments, the curing of step d) and/or (f) is conducted such that at least about 20%, or at least about 40%, or at least about 75%, or about 100% of the polyethylene oxide melts.

In certain embodiments, the process of manufacture comprises a curing step (f), and no curing step (d).

In certain embodiments, the process as described above comprises a further step (g) of coating the optionally cured core-shell structure (e.g., by coating the second matrix formulation).

In certain such embodiments, the coating is a film coating (e.g., a cosmetic film coating, such as an Opadry® coating).

In certain embodiments, an initial film coating or a fraction of a film coating is applied prior to performing curing step (d) and/or (f). This film coating provides an "overcoat" for the matrix formulations to function as an anti-tacking agent, i.e., to avoid that the matrix formulations stick together. In certain such embodiments the film coating which is applied prior to the curing step is an Opadry® film coating. After the curing step (f), a further film coating step can be performed.

The invention is also directed to a solid oral extended release pharmaceutical dosage form obtained by a process as described herein.

Adjustment of In Vitro Release Profiles

In certain embodiments, the invention is directed to the use of a core-shell structure comprising an amount of an active agent (A) and an amount of an active agent (B), wherein said core-shell structure comprises
(1) a core comprising a first matrix formulation,
the first matrix formulation comprising at least one active agent selected from active agent (A) and active agent (B), and
(2) a shell encasing the core and consisting of a second matrix formulation,
wherein the weight ratio of the first matrix formulation to the second matrix formulation is from about 1:10 to about 4:1,
in a solid oral extended release dosage form, for independently adjusting the in vitro release profiles of the active agent (A) and the active agent (B) from said dosage form.

The in vitro release profiles of the active agent (A) and the active agent (B) from said dosage form can be independently adjusted by distributing the amount of active agent (A) between the first and the second matrix formulation, and distributing the amount of active agent (B) between the first and the second matrix formulation (e.g., such that a core-shell structure belonging to one of the embodiments #1 to #8 is realized, and/or by realizing one of the above described weight ratios of the active agent (A) in the first matrix formulation to the active agent (A) in the second matrix formulation, and/or by realizing one of the above described weight ratios of the active agent (B) in the first matrix formulation to the active agent (B) in the second matrix formulation). For a dosage form with a given total amount of active agent (A) and active agent (B), the in vitro release profiles of the active agent (A) and the active agent (B) from said dosage form can additionally be adjusted, e.g., by modifying the weight ratio of the first matrix formulation to the second matrix formulation (e.g., by realizing one of the weight ratios as described above), by modifying the materials used for the first and the second matrix formulation and their respective weight-% amounts, etc.

In certain embodiments, the use of the core-shell structure is in a solid oral extended release dosage form with the features as described herein.

In certain embodiments, the invention is directed to a method of independently adjusting the in vitro release profiles of an active agent (A) and an active agent (B) from a solid oral extended release dosage form, comprising
preparing a core-shell structure comprising an amount of the active agent (A) and an amount of the active agent (B), wherein the core-shell structure comprises
(1) a core comprising a first matrix formulation, and
(2) a shell encasing the core and consisting of a second matrix formulation,
wherein the weight ratio of the first matrix formulation to the second matrix formulation is from about 1:10 to about 4:1,
wherein the amount of active agent (A) is distributed between the first and the second matrix formulation, and the amount of active agent (B) is distributed between the first and the second matrix formulation, such that the first matrix formulation comprises at least one active agent selected from active agent (A) and active agent (B), and
providing said dosage form with said core-shell structure.

In certain embodiments, the solid oral extended release dosage form is a solid oral extended release dosage form with the features as described herein.

Methods of Treatment

Depending upon the nature (and efficacy) of the active agents incorporated therein, the solid dosage forms of the invention can be used to treat or prevent various conditions or diseases. For example, when the solid dosage forms include one or more anticancer agents, the solid dosage forms are useful for treating or preventing a cancer (or, preventing or inhibiting the maturation and proliferation of a neoplasm), which the anticancer agent has been proven to be efficacious. Likewise, when the solid dosage forms include one or more CNS stimulants (e.g., amphetamine, and methylphenidate), the solid dosage forms are useful for boosting brain activities in a patient, thereby treating conditions including such as, attention deficit hyperactivity disorder (ADHD) and narcolepsy.

In certain embodiments, the solid dosage forms of the invention include at least an analgesic (e.g., opioid or non-opioid analgesics). Thus, certain aspects of the invention provide a method of treating or preventing pain comprising administering to a patient identified in need thereof a solid oral extended release dosage form as described herein, wherein at least one of the active agents an analgesic. In one embodiment, the active agent (A) is an opioid analgesic.

In certain embodiments, the invention is directed to a solid oral extended release dosage form as described herein for use in a method of treating or preventing pain.

In one embodiment, the invention is directed to the use of a solid oral extended release dosage form as described herein for the manufacture of a medicament for treating or preventing pain.

In separate embodiments, the solid dosage forms of this invention contain an opioid analgesic and buprenorphine as the active agents. In certain embodiments, these solid dosage forms are useful for treating or preventing pain in a patient with reduced opioid-induced adverse pharmacodynamic responses. In other embodiments, the dosage forms of this invention are useful for treating or preventing one or more reduced opioid-induced adverse pharmacodynamic responses in a patient.

The opioid-induced adverse pharmacodynamic response is selected from the group consisting of bowel dysfunction, nausea, vomiting, somnolence, dizziness, respiratory depression, headache, dry mouth, sedation, sweats, asthenia, hypotension, dysphoria, delirium, miosis, pruritus, urticaria, urinary retention, allodynia, physical dependence and tolerance. In certain embodiments, the buprenorphine is included in a therapeutically effective amount. In some embodiments, the buprenorphine included in the solid dosage form is in the sub-analgesic amount.

The disclosures on benefits and/or uses associated with certain solid dosage forms of the invention can be found in US Patent Publication No. 2016/0106735 A1 and PCT Publication No. WO2013156850 A1, both of which are incorporated herein by their entireties.

Examples

The invention will now be more fully described with reference to the accompanying examples. It should be understood, however, that the following description is illustrative only and should not be taken in any way as a restriction of the invention.

Materials and General Information

For the manufacture of tablets according to Examples 1-17 below, the following materials were used:

| Material | Manufacturer/supplier | Lot Number(s) |
|---|---|---|
| Oxycodone hydrochloride[1] | Rhodes Technologies | 29-12 XYK |
| Buprenorphine | Noramco/Rhodes | 15JN140-4 (Noramco) |

-continued

| Material | Manufacturer/supplier | Lot Number(s) |
|---|---|---|
| hydrochloride | | 4-15BUH (Rhodes) |
| Polyethylene Oxide NF (POLYOX @ WSR-301, LEO) | Dow Chemical | D682F6HPB3 2I1701DLBS (FP grade) |
| Polyethylene Oxide NF (POLYOX @ WSR N-10) | Dow Chemical | ZL2955S5H3 |
| Magnesium Stearate[2] | Peter Greven | C302873 |

[1]According to the certificate of analysis, the oxycodone HCl material used for Examples 1-17 below has a water content of 5.2% + residual solvent 0.08% + total impurities 0.2%, which sums up to 5.48 (weight-)% in total. Accordingly, an adjustment factor can be calculated as follows: 100% − 5.48% = 94.52% = 0.9452;
[2]non-bovine In the tables given below, which specify the composition of the tablets according to Examples 1-17, the respective column "Target mg/unit"
  refers to the amount of pure oxycodone hydrochloride (Mw=351.82 g/mol); and
  expresses the amount of buprenorphine hydrochloride as the equivalent amount of buprenorphine base (1 mg of buprenorphine HCl corresponding to 0.93 mg of buprenorphine base).

By contrast, the respective column "Formulation (mg/unit)" indicates the actual formulation and
  refers to the amount of oxycodone hydrochloride material (mg/unit) to be actually used to reach the target mg/unit of pure oxycodone hydrochloride (Mw=351.82 g/mol), which is calculated by applying the above indicated adjustment factor of 0.9452; and
  indicates the amount of buprenorphine hydrochloride (mg/unit) to be actually used.

Whenever the below tables refer to the "weight ratio oxycodone$_{total}$/buprenorphine$_{total}$", the weight ratio of the total amount of oxycodone in the tablet to the total amount of buprenorphine in the tablet is meant, calculated with the total amount of oxycodone in the tablet expressed as the equimolar amount of oxycodone hydrochloride (Mw=351.82 g/mol) in mg and the total amount of buprenorphine in the tablet expressed as the equimolar amount of buprenorphine base (Mw=467.64 g/mol) in mg.

The In vitro dissolution testing of the tablets according to Examples 1-17 below was performed as follows: Tablets (uncured, or cured for a time period as indicated) were tested in vitro using a USP Apparatus 1 (basket) at 100 rpm in 900 ml simulated gastric fluid without enzymes (SGF) at 37.0±0.5° C. In order to reduce the propensity of the tablets, once hydrated in the dissolution medium, to stick to the solid underside of the top of the basket or the base of the shaft, a retaining spring (passivized stainless steel 316 spring, 1.5-cm outside diameter and 2-cm length) was placed in the upper part of the basket (above the tablet). Sampling time points included 0.5, 1.0, 2.0, 4.0, 8.0, 12.0 and 18.0 hours (or as indicated). The samples were analyzed by reversed-phase high performance liquid chromatography (HPLC) on Waters XBridge phenyl, 4.6×75 mm, 3.5 pm column maintained at 60° C. using a gradient method with mobile phase consisting of acetonitrile and potassium phosphate monobasic and ammonium hexafluorophosphate buffer with UV detection at 285 nm and 212 nm.

Example 1

In Example 1, tablets comprising oxycodone hydrochloride in the core and buprenorphine hydrochloride in the shell and having the composition as shown in Tables 1.1 and 1.2 were prepared.

TABLE 1

| Core | Target mg/unit | Formulation (mg/unit) | Formulation (weight-%) |
|---|---|---|---|
| Oxycodone HCl | 10.00 | 10.58 | 7.05 |
| Buprenorphine HCl | 0.00 | 0.00 | 0.00 |
| Polyethylene Oxide POLYOX ® WSR-301 | ad 150.00 | 137.92 | 91.95 |
| Magnesium Stearate | 1.50 | 1.50 | 1.00 |
| Total core | 150.00 | 150.00 | 100.00 |

| Shell | Target mg/unit | Formulation (mg/unit) | Formulation (weight-%) |
|---|---|---|---|
| Oxycodone HCl | 0.00 | 0.00 | 0.00 |
| Buprenorphine HCl | 0.50[1] | 0.54 | 0.27 |
| Polyethylene Oxide POLYOX ® WSR N-10 | ad 200.00 | 197.96 | 98.98 |
| Magnesium Stearate | 1.50 | 1.50 | 0.75 |
| Total shell | 200.00 | 200.00 | 100.00 |

[1] expressed as equivalent amount of buprenorphine base

TABLE 1.2

| Core + Shell | Target mg/unit | Weight ratios | |
|---|---|---|---|
| Oxycodone HCl | 10.00 | | |
| Buprenorphine HCl | 0.50 | | |
| | | Weight ratio oxycodone:buprenorphine[1]: | 20 |
| Total weight core + shell | 350.00 | Weight ratio core/shell | 0.75 |

[1] expressed as equivalent amount of buprenorphine base

The processing steps to manufacture tablets of Example 1 were as follows:

Preparation of core blend:
1. Polyethylene oxide (POLYOX® WSR-301) was weighed and transferred into a 20 mL disposable scintillation vial. An individual vial was used for each preparation.
2. The active(s) and magnesium stearate were weighed and transferred into the scintillation vial of step 1.
3. The materials in the scintillation vial were vortexed for 15 seconds to yield the core blend.

Preparation of shell blend:
4. Polyethylene oxide (POLYOX® WSR N-10) was weighed and transferred into a 20 mL disposable scintillation vial. An individual vial was used for each preparation.
5. The active(s) and magnesium stearate were weighed and transferred into the scintillation vial of step 4.
6. The materials in the scintillation vial were vortexed for 15 seconds to yield the shell blend.

Preparation of core tablet:
7. The core blend was discharged onto a weighing paper (tapping the scintillation vial with a spatula to dispense as much of the core blend as possible).
8. A Carver Press was setup with 9/32 inch unmarked, round concave tooling.
9. The core blend was transferred into the die and compressed by applying a compression force of 1500-1700 lbs[1] to yield the core tablet.

Preparation of core-shell tablet(s):
10. The shell blend was discharged onto a weighing paper (tapping the scintillation vial with a spatula to dispense as much of the shell blend as possible).
11. A Carver Press was set up with 3/8 inch, round concave tooling.
12. Approximately half of the amount of the shell blend was transferred into the die.
13. The core tablet of step 9 was placed into the center of the die containing half of the amount of the shell blend.
14. The remaining amount of the shell blend was transferred into the die to cover the sides and the top of the core tablet.
15. Subsequently the shell blend was compressed by applying a compression force of 1000-1200 lbs to yield the core-shell tablet.
16. Steps 1 to 15 were repeated to yield several core-shell tablets.

Curing
17. For curing, core-shell tablets were placed on a mesh screen and cured in a preheated gravity-flow convection oven at a temperature of 70° C. for 30 minutes.

The results of the in vitro dissolution testing of tablets of Example 1 are shown in Table 1.3 and in FIG. 1. The indicated values are an average of three measurements.

TABLE 1.3

In vitro dissolution results for Example 1

| | Dissolution time [hours] | | | | | | |
|---|---|---|---|---|---|---|---|
| | 0.5 | 1 | 2 | 4 | 8 | 12 | 18 |
| % oxycodone HCl released | 1 | 6 | 22 | 48 | 78 | 89 | 93 |
| % buprenorphine HCl released | 28 | 54 | 71 | 69 | 68 | 71 | 79 |

| | Thickness (mm) | Diameter (mm) |
|---|---|---|
| Core tablet | 3.99 | 7.09 |
| Core-Shell tablet before curing | 5.32 | 9.41 |
| Core-Shell tablet after curing | 5.88 | 9.55 |

[1] 1 lb. = 1 pound = 0.45359237 kg

Example 2

In Example 2, tablets comprising oxycodone hydrochloride and buprenorphine hydrochloride both in the core and in the shell and having the composition as shown in Tables 2.1 and 2.2 were prepared.

TABLE 2.1

| Core | Target mg/unit | Formulation (mg/unit) | Formulation (weight-%) |
|---|---|---|---|
| Oxycodone HCl | 7.500 | 7.93 | 5.29 |
| Buprenorphine HCl | 0.125[1] | 0.13 | 0.09 |
| Polyethylene Oxide POLYOX ® WSR-301 | ad 150.000 | 140.44 | 93.63 |
| Magnesium Stearate | 1.500 | 1.50 | 1.00 |
| Total core | 150.000 | 150.00 | 100.00 |

TABLE 2.1-continued

| Shell | Target mg/unit | Formulation (mg/unit) | Formulation (weight-%) |
|---|---|---|---|
| Oxycodone HCl | 2.500 | 2.64 | 1.32 |
| Buprenorphine HCl | 0.375 | 0.40 | 0.20 |
| Polyethylene Oxide POLYOX ® WSR N-10 | ad 200.000 | 195.46 | 97.73 |
| Magnesium Stearate | 1.500 | 1.50 | 0.75 |
| Total shell | 200.000 | 200.00 | 100.00 |

[1] expressed as equivalent amount of buprenorphine base

TABLE 2.2

| Core + Shell | Target mg/unit | Weight ratios | |
|---|---|---|---|
| Oxycodone HCl | 10.00 | Weight ratio oxycodone $HCl_{core}$/oxycodone $HCl_{shell}$ | 3 |
| Buprenorphine HCl | 0.50[1] | Weight ratio buprenorphine $HCl_{core}$/buprenorphine $HCl_{shell}$ | 0.33 |
| | | Weight ratio $oxycodone_{total}$/$buprenorphine_{total}$ | 20 |
| Total weight core + shell | 350.00 | Weight ratio core/shell | 0.75 |

[1] expressed as equivalent amount of buprenorphine base

The processing steps to manufacture tablets of Example 2 correspond to the process of manufacture (steps 1 to 17) as described for Example 1.

Figure 2:
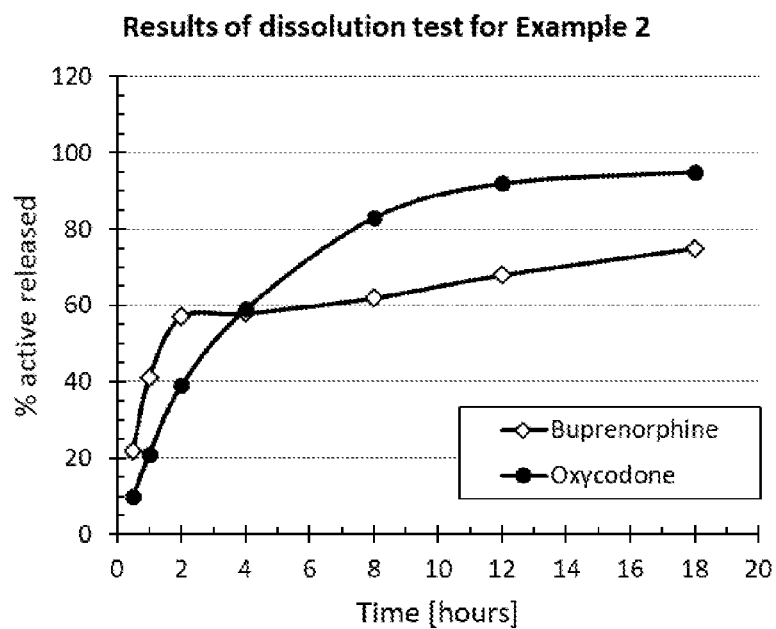
FIG. 2 is a graph depicting the results of the in vitro dissolution test of tablets according to Example 2.

The results of the in vitro dissolution testing of tablets of Example 2 are shown in Table 2.3 and in FIG. 2. The indicated values are an average of three measurements.

TABLE 2.3

In vitro dissolution results for Example 2

| | Dissolation time [hours] | | | | | | |
|---|---|---|---|---|---|---|---|
| | 0.5 | 1 | 2 | 4 | 8 | 12 | 18 |
| % oxycodone HCl released | 10 | 21 | 39 | 59 | 83 | 92 | 95 |
| % buprenorphine HCl released | 22 | 41 | 57 | 58 | 62 | 68 | 75 |

| | Thickness (mm) | Diameter (mm) |
|---|---|---|
| Core tablet | 4.11 | 7.10 |
| Core-Shell tablet before curing | 5.30 | 9.40 |
| Core-Shell tablet after curing | 5.97 | 9.55 |

Example 3

In Example 3, tablets comprising oxycodone hydrochloride and buprenorphine hydrochloride both in the core and in the shell and having the composition as shown in Tables 3.1 and 3.2 were prepared.

TABLE 3.1

| Core | Target mg/unit | Formulation (mg/unit) | Formulation (weight-%) |
|---|---|---|---|
| Oxycodone HCl | 60.00 | 63.48 | 25.39 |
| Buprenorphine HCl | 4.00[1] | 4.30 | 1.72 |
| Polyethylene Oxide POLYOX ® WSR-301 | ad 250.00 | 179.72 | 71.89 |
| Magnesium Stearate | 2.50 | 2.50 | 1.00 |
| Total core | 250.00 | 250.00 | 100.00 |

| Shell | Target mg/unit | Formulation (mg/unit) | Formulation (weight-%) |
|---|---|---|---|
| Oxycodone HCl | 20.00 | 21.16 | 7.05 |
| Buprenorphine HCl | 12.00 | 12.90 | 4.30 |
| Polyethylene Oxide POLYOX ® WSR N-10 | ad 300.00 | 263.44 | 87.81 |
| Magnesium Stearate | 2.50 | 2.50 | 0.83 |
| Total shell | 300.00 | 300.00 | 100.00 |

[1] expressed as equivalent amount of buprenorphine base

TABLE 3.2

| Core + Shell | Target mg/unit | Weight ratios | |
|---|---|---|---|
| Oxycodone HCl | 80.00 | Weight ratio oxycodone $HCl_{core}$/oxycodone $HCl_{shell}$ | 3 |
| Buprenorphine HCl | 16.00[1] | Weight ratio buprenorphine $HCl_{core}$/buprenorphine $HCl_{shell}$ | 0.33 |
| | | Weight ratio $oxycodone_{total}$/$buprenorphine_{total}$ | 5 |
| Total weight core + shell | 550.00 | Weight ratio core/shell | 0.83 |

[1] expressed as equivalent amount of buprenorphine base

The processing steps to manufacture tablets of Example 3 correspond to the process of manufacture (steps 1 to 17) as described for Example 1, with the following particulars:

In step 8, 11/32 inch, round concave tooling was used.

In step 11, 15/32 inch, round concave tooling was used.

Figure 3:
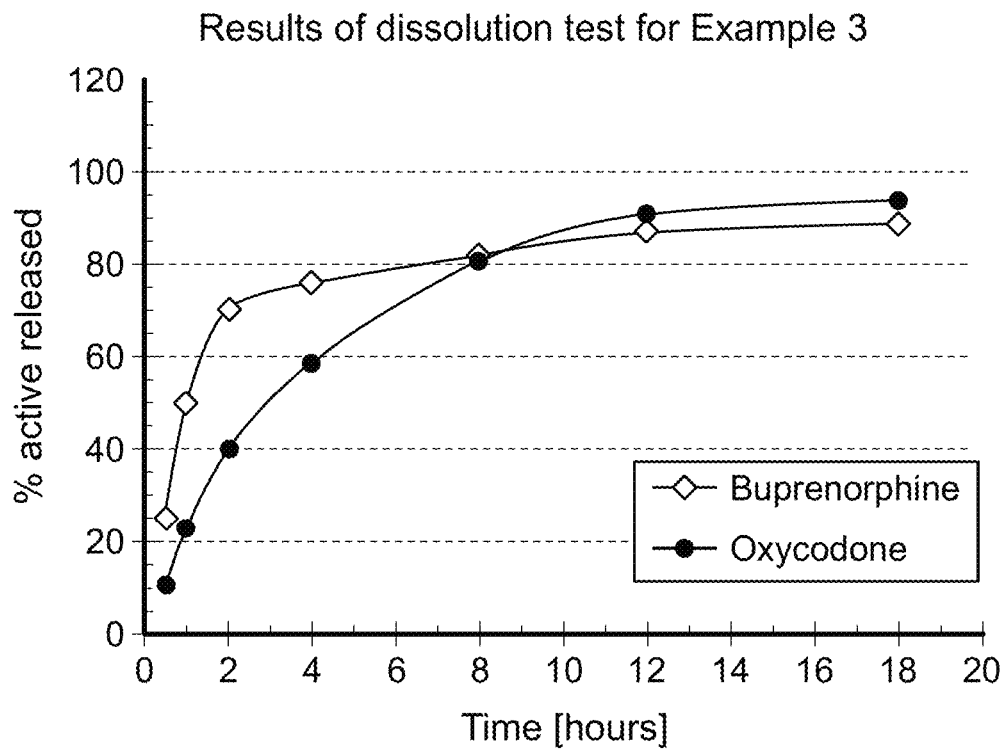
FIG. 3 is a graph depicting the results of the in vitro dissolution test of tablets according to Example 3.

The results of the in vitro dissolution testing of tablets of Example 3 are shown in Table 3.3 and in FIG. 3. The indicated values are an average of three measurements.

TABLE 3.3

In vitro dissolution results for Example 3

| | Dissolution time [hours] | | | | | | |
|---|---|---|---|---|---|---|---|
| | 0.5 | 1 | 2 | 4 | 8 | 12 | 18 |
| % oxycodone HCl released | 11 | 23 | 40 | 59 | 81 | 91 | 94 |
| % buprenorphine HCl released | 25 | 50 | 70 | 76 | 82 | 87 | 89 |

| | Thickness (mm) | Diameter (mm) |
|---|---|---|
| Core tablet | 4.26 | 8.75 |
| Core-Shell tablet before curing | 5.96 | 11.88 |
| Core-Shell tablet after curing | 6.40 | 11.38 |

Example 4

In Example 4, tablets comprising oxycodone hydrochloride and buprenorphine hydrochloride both in the core and in the shell and having the composition as shown in Tables 4.1 and 4.2 were prepared.

TABLE 4.1

| Core | Target mg/unit | Formulation (mg/unit) | Formulation (weight-%) |
|---|---|---|---|
| Oxycodone HCl | 72.00 | 76.17 | 30.47 |
| Buprenorphine HCl | 1.60 | 1.72 | 0.69 |
| Polyethylene Oxide POLYOX ® WSR-301 | ad 250.00 | 169.61 | 67.84 |
| Magnesium Stearate | 2.50 | 2.50 | 1.00 |
| Total core | 250.00 | 250.00 | 100.00 |

| Shell | Target mg/unit | Formulation (mg/unit) | Formulation (weight-%) |
|---|---|---|---|
| Oxycodone HCl | 8.00 | 8.46 | 2.82 |
| Buprenorphine HCl | 14.40[1] | 15.48 | 5.16 |
| Polyethylene Oxide POLYOX ® WSR N-10 | ad 300.00 | 273.56 | 91.19 |
| Magnesium Stearate | 2.50 | 2.50 | 0.83 |
| Total shell | 300.00 | 300.00 | 100.00 |

[1] expressed as equivalent amount of buprenorphine base

TABLE 4.2

| Core + Shell | Target mg/unit | Weight ratios | |
|---|---|---|---|
| Oxycodone HCl | 80.00 | Weight ratio oxycodone HCl$_{core}$/oxycodone HCl$_{shell}$ | 9 |
| Buprenorphine HCl | 16.00[1] | Weight ratio buprenorphine HCl$_{core}$/buprenorphine HCl$_{shell}$ | 0.11 |
| | | Weight ratio oxycodone$_{total}$/buprenorphine$_{total}$ | 5 |
| Total weight core + shell | 550.00 | Weight ratio core/shell | 0.83 |

[1] expressed as equivalent amount of buprenorphine base

The processing steps to manufacture tablets of Example 4 correspond to the process of manufacture (steps 1 to 17) as described for Example 3.

Figure 4:
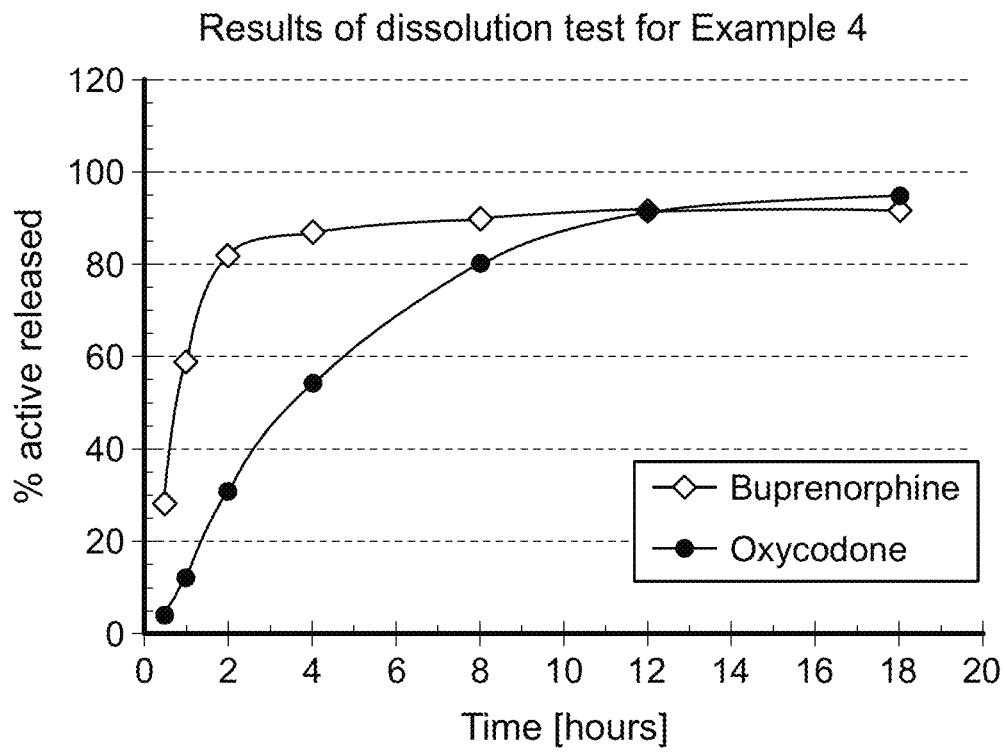
FIG. 4 is a graph depicting the results of the in vitro dissolution test of tablets according to Example 4.

The results of the in vitro dissolution testing of tablets of Example 4 are shown in Table 4.3 and in FIG. 4. The indicated values are an average of three measurements.

TABLE 4.3

| In vitro dissolution results for Example 4 | | | | | | |
|---|---|---|---|---|---|---|
| Dissolution time [hours] | 0.5 | 1 | 2 | 4 | 8 | 12 | 18 |
| % oxycodone HCl released | 4 | 12 | 31 | 54 | 80 | 91 | 95 |
| % buprenorphine HCl released | 28 | 59 | 82 | 87 | 90 | 92 | 92 |

| | Thickness (mm) | Diameter (mm) |
|---|---|---|
| Core tablet | 4.38 | 8.80 |
| Core-Shell tablet before curing | 5.98 | 11.87 |
| Core-Shell tablet after curing | 6.44 | 11.35 |

Example 5

In Example 5, tablets comprising oxycodone hydrochloride and buprenorphine hydrochloride both in the core and in the shell and having the composition as shown in Tables 5.1 and 5.2 were prepared.

TABLE 5.1

| Core | Target mg/unit | Formulation (mg/unit) | Formulation (weight-%) |
|---|---|---|---|
| Oxycodone HCl | 30.00 | 31.74 | 21.16 |
| Buprenorphine HCl | 2.00[1] | 2.15 | 1.43 |
| Polyethylene Oxide POLYOX ® WSR-301 | ad 150.00 | 114.61 | 76.41 |
| Magnesium Stearate | 1.50 | 1.50 | 1.00 |
| Total core | 150.00 | 150.00 | 100.00 |

| Shell | Target mg/unit | Formulation (mg/unit) | Formulation (weight-%) |
|---|---|---|---|
| Oxycodone HCl | 10.00 | 10.58 | 5.29 |
| Buprenorphine HCl | 6.00 | 6.45 | 3.23 |
| Polyethylene Oxide POLYOX ® WSR N-10 | ad 200.00 | 181.47 | 90.74 |
| Magnesium Stearate | 1.50 | 1.50 | 0.75 |
| Total shell | 200.00 | 200.00 | 100.00 |

[1] expressed as equivalent amount of buprenorphine base

TABLE 5.2

| Core + Shell | Target mg/unit | Weight ratios | |
|---|---|---|---|
| Oxycodone HCl | 40.00 | Weight ratio oxycodone HCl$_{core}$/oxycodone HCl$_{shell}$ | 3 |
| Buprenorphine HCl | 8.00[1] | Weight ratio buprenorphine HCl$_{core}$/buprenorphine HCl$_{shell}$ | 0.33 |
| | | Weight ratio oxycodone$_{total}$/buprenorphine$_{total}$ | 5 |
| Total weight core + shell | 350.00 | Weight ratio core/shell | 0.75 |

[1] expressed as equivalent amount of buprenorphine base

The processing steps to manufacture tablets of Example 5 correspond to the process of manufacture (steps 1 to 17) as described for Example 1, with the following particulars:

In step 9, a compression force of 1000-1200 lbs was applied.

In step 15, a compression force of 1800-2000 lbs was applied.

Figure 5:
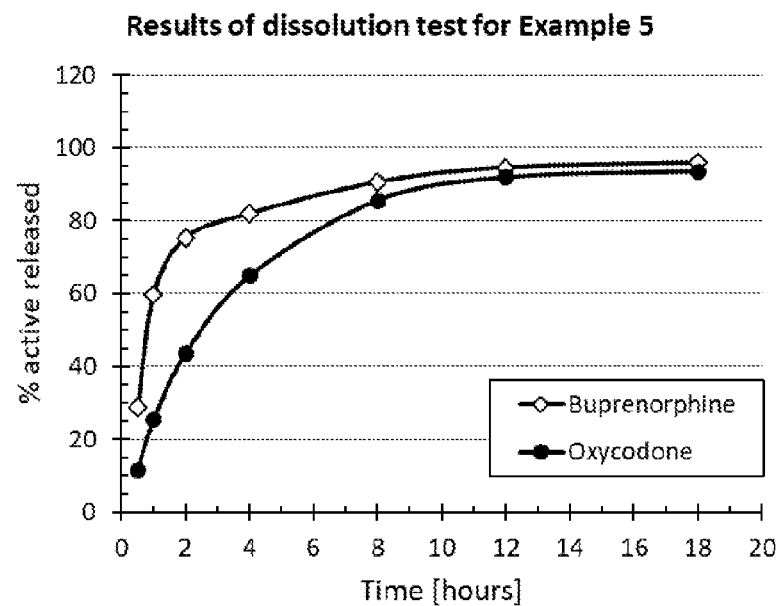
FIG. 5 is a graph depicting the results of the in vitro dissolution test of tablets according to Example 5.

The results of the in vitro dissolution testing of tablets of Example 5 are shown in Table 5.3 and in FIG. 5. The indicated values are an average of three measurements.

TABLE 5.3

| In vitro dissolution results for Example 5 | | | | | | | |
|---|---|---|---|---|---|---|---|
| Dissolution time [hours] | 0.5 | 1 | 2 | 4 | 8 | 12 | 18 |
| % oxycodone HCl released | 12 | 25 | 44 | 65 | 86 | 92 | 94 |
| % buprenorphine HCl released | 29 | 60 | 75 | 82 | 91 | 95 | 96 |

| | Weight (mg) | Thickness (mm) | Diameter (mm) |
|---|---|---|---|
| Core tablet | 147.5 | 4.04 | 7.12 |
| Core-Shell tablet before curing | 341.4 | 5.18 | 9.46 |
| Core-Shell tablet after curing | 339.5 | 5.73 | 9.25 |

Example 6

In Example 6, tablets comprising oxycodone hydrochloride and buprenorphine hydrochloride both in the core and in the shell and having the composition as shown in Tables 6.1 and 6.2 were prepared.

TABLE 6.1

| Core | Target mg/unit | Formulation (mg/unit) | Formulation (weight-%) |
|---|---|---|---|
| Oxycodone HCl | 30.00 | 31.74 | 21.16 |
| Buprenorphine HCl | 2.00[1] | 2.15 | 1.43 |
| Polyethylene Oxide POLYOXO ® WSR-301 | ad 150.00 | 114.61 | 76.41 |
| Magnesium Stearate | 1.50 | 1.50 | 1.00 |
| Total core | 150.00 | 150.00 | 100.00 |

| Shell | Target mg/unit | Formulation (mg/unit) | Formulation (weight-%) |
|---|---|---|---|
| Oxycodone HCl | 10.00 | 10.58 | 4.23 |
| Buprenorphine HCl | 6.00 | 6.45 | 2.58 |
| Polyethylene Oxide POLYOX ® WSR N-10 | ad 250.00 | 231.47 | 92.59 |
| Magnesium Stearate | 1.50 | 1.50 | 0.60 |
| Total shell | 250.00 | 250.00 | 100.00 |

[1]expressed as equivalent amount of buprenorphine base

TABLE 6.2

| Core + Shell | Target mg/unit | Weight ratios | |
|---|---|---|---|
| Oxycodone HCl | 40.00 | Weight ratio oxycodone HCl$_{core}$/ oxycodone HCl$_{shell}$ | 3 |
| Buprenorphine HCl | 8.00[1] | Weight ratio buprenorphine HCl$_{core}$/ buprenorphine HCl$_{shell}$ | 0.33 |
| | | Weight ratio oxycodone$_{total}$/ buprenorphine$_{total}$ | 5 |
| Total weight core + shell | 400.00 | Weight ratio core/shell | 0.6 |

[1]expressed as equivalent amount of buprenorphine base

The processing steps to manufacture tablets of Example 6 correspond to the process of manufacture (steps 1 to 17) as described for Example 5.

Figure 6:
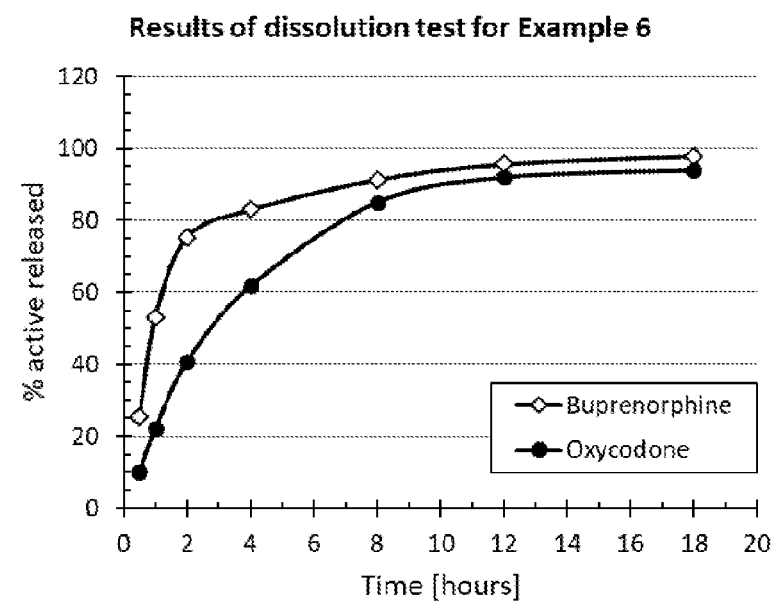
FIG. 6 is a graph depicting the results of the in vitro dissolution test of tablets according to Example 6.

The results of the in vitro dissolution testing of tablets of Example 6 are shown in Table 6.3 and in FIG. 6. The indicated values are an average of three measurements.

TABLE 6.3

| In vitro dissolution results for Example 6 | | | | | | | |
|---|---|---|---|---|---|---|---|
| Dissolution time [hours] | 0.5 | 1 | 2 | 4 | 8 | 12 | 18 |
| % oxyendone HCl released | 10 | 22 | 41 | 62 | 85 | 92 | 94 |
| % buprenorphine HCl released | 25 | 53 | 75 | 83 | 91 | 96 | 98 |

| | Weight (mg) | Thickness (mm) | Diameter (mm) |
|---|---|---|---|
| Core tablet | 146.7 | 4.05 | 7.12 |
| Core-Shell tablet before caring | 394.2 | 5.82 | 9.48 |
| Core-Shell tablet after curing | 392.3 | 6.35 | 9.24 |

Example 7

In Example 7, tablets comprising oxycodone hydrochloride and buprenorphine hydrochloride both in the core and in the shell and having the composition as shown in Tables 7.1 and 7.2 were prepared.

TABLE 7.1

| Core | Target mg/unit | Formulation (mg/unit) | Formulation (weight-%) |
|---|---|---|---|
| Oxycodone HCl | 30.00 | 31.74 | 31.74 |
| Buprenorphine HCl | 2.00[1] | 2.15 | 2.15 |
| Polyethylene Oxide POLYOX ® WSR-301 | ad 100.00 | 64.61 | 64.61 |
| Magnesium Stearate | 1.50 | 1.50 | 1.50 |
| Total core | 100.00 | 100.00 | 100.00 |

| Shell | Target mg/unit | Formulation | Formulation (weight-%) |
|---|---|---|---|
| Oxycodone HCl | 10.00 | 10.58 | 3.53 |
| Buprenorphine HCl | 6.00 | 6.45 | 2.15 |
| Polyethylene Oxide POLYOX ® WSR N-10 | ad 300.00 | 281.47 | 93.82 |
| Magnesium Stearate | 1.50 | 1.50 | 0.50 |
| Total shell | 300.00 | 300.00 | 100.00 |

[1]expressed as equivalent amount of buprenorphine base

TABLE 7.2

| Core + Shell | Target mg/unit | Weight ratios | |
|---|---|---|---|
| Oxycodone HCl | 40.00 | Weight ratio oxycodone HCl$_{core}$/oxycodone HCl$_{shell}$ | 3 |
| Buprenorphine HCl | 8.00[1] | Weight ratio buprenorphine HCl$_{core}$/buprenorphine HCl$_{shell}$ | 0.33 |
| | | Weight ratio oxycodone$_{total}$/buprenorphine$_{total}$ | 5 |
| Total weight core + shell | 400.00 | Weight ratio core/shell | 0.33 |

[1]expressed as equivalent amount of buprenorphine base

The processing steps to manufacture tablets of Example 7 correspond to the process of manufacture (steps 1 to 17) as described for Example 5.

Figure 7:
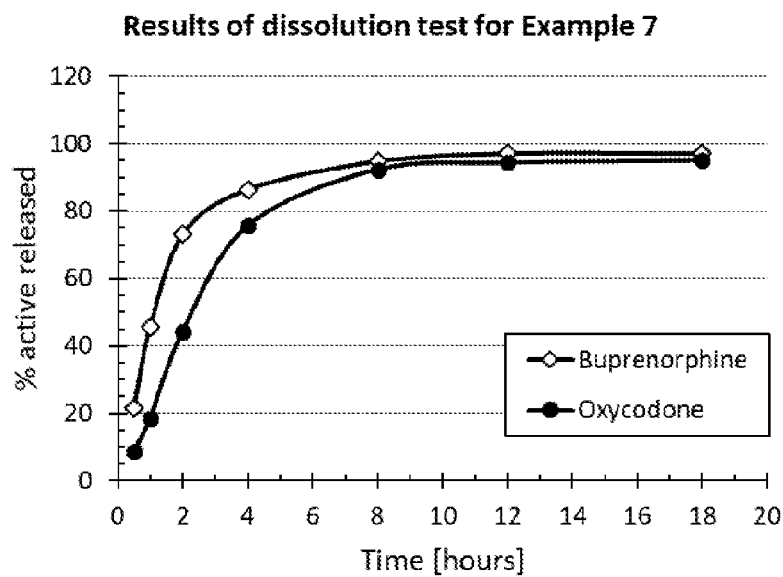
FIG. 7 is a graph depicting the results of the in vitro dissolution test of tablets according to Example 7.

The results of the in vitro dissolution testing of tablets of Example 7 are shown in Table 7.3 and in FIG. 7. The indicated values are an average of three measurements.

TABLE 7.3

| In vitro dissolution results for Example 7 | | | | | | |
|---|---|---|---|---|---|---|
| Dissolution time [hours] | 0.5 | 1 | 2 | 4 | 8 | 12 | 18 |
| % oxycodone HCl released | 9 | 19 | 44 | 76 | 92 | 94 | 95 |
| % buprenorplane HCl released | 22 | 46 | 73 | 86 | 95 | 97 | 97 |

| | Weight (mg) | Thickness (mm) | Diameter (mm) |
|---|---|---|---|
| Core tablet | 96.7 | 2.96 | 7.14 |
| Core-Shell tablet before curing | 393.6 | 5.74 | 9.49 |
| Core-Shell tablet after curing | 391.7 | 6.04 | 9.36 |

Example 8

In Example 8, tablets comprising oxycodone hydrochloride and buprenorphine hydrochloride both in the core and in the shell and having the composition as shown in Tables 8.1 and 8.2 were prepared.

TABLE 8.1

| Core | Target mg/unit | Formulation (mg/unit) | Formulation (weight-%) |
|---|---|---|---|
| Oxycodone HCl | 36.00 | 38.09 | 25.39 |
| Buprenorphine HCl | 0.80[1] | 0.86 | 0.57 |
| Polyethylene Oxide POLYOX ® WSR-301 | ad 150.00 | 109.55 | 73.03 |
| Magnesium Stearate | 1.50 | 1.50 | 1.00 |
| Total core | 150.00 | 150.00 | 100.00 |

| Shell | Target mg/unit | Formulation (mg/unit) | Formulation (weight-%) |
|---|---|---|---|
| Oxycodone HCl | 4.00 | 4.23 | 1.69 |
| Buprenorphine HCl | 7.20[1] | 7.74 | 3.10 |
| Polyethylene Oxide POLYOX ® WSR N-10 | ad 250.00 | 236.53 | 94.61 |
| Magnesium Stearate | 1.50 | 1.50 | 0.60 |
| Total shell | 250.00 | 250.00 | 100.00 |

[1]expressed as equivalent amount of buprenorphine base

TABLE 8.2

| Core + Shell | Target mg/unit | Weight ratios | |
|---|---|---|---|
| Oxycodone HCl | 40.00 | Weight ratio oxycodone HCl$_{core}$/oxycodone HCl$_{shell}$ | 9 |
| Buprenorphine HCl | 8.00[1] | Weight ratio buprenorphine HCl$_{core}$/buprenorphine HCl$_{shell}$ | 0.11 |
| | | Weight ratio oxycodone$_{total}$/buprenorphine$_{total}$ | 5 |
| Total weight core + shell | 400.00 | Weight ratio core/shell | 0.6 |

[1]expressed as equivalent amount of buprenorphine base

The processing steps to manufacture tablets of Example 8 correspond to the process of manufacture (steps 1 to 17) as described for Example 5.

Figure 8:
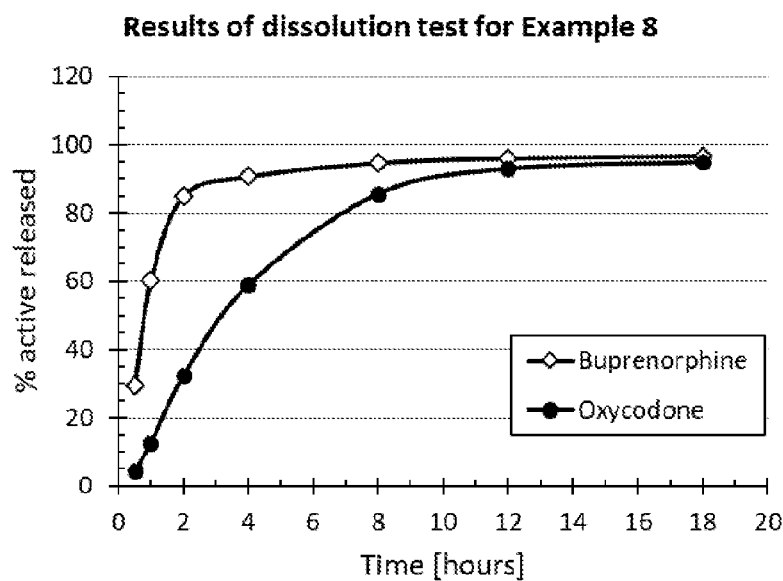
FIG. 8 is a graph depicting the results of the in vitro dissolution test of tablets according to Example 8.

The results of the in vitro dissolution testing of tablets of Example 8 are shown in Table 8.3 and in FIG. 8. The indicated values are an average of three measurements.

TABLE 8.3

| In vitro dissolution results for Example 8 | | | | | | | |
|---|---|---|---|---|---|---|---|
| Dissolution time [hours] | 0.5 | 1 | 2 | 4 | 8 | 12 | 18 |
| % oxycodone HCl released | 4 | 13 | 32 | 59 | 86 | 93 | 95 |
| % buprenorphine HCl released | 29 | 60 | 85 | 91 | 95 | 96 | 97 |

| | Weight (mg) | Thickness (mm) | Diameter (mm) |
|---|---|---|---|
| Core tablet | 146.9 | 4.03 | 7.12 |
| Core-Shell tablet before curing | 394.0 | 5.85 | 9.48 |
| Core-Shell tablet after curing | 391.9 | 6.38 | 9.24 |

Example 9

In Example 9, tablets comprising oxycodone hydrochloride and buprenorphine hydrochloride both in the core and in the shell and having the composition as shown in Tables 9.1 and 9.2 were prepared.

TABLE 9.1

| Core | Target mg/unit | Formulation (mg/unit) | Formulation (weight-%) |
|---|---|---|---|
| Oxycodone HCl | 30.00 | 31.74 | 21.16 |
| Bupreporphine HCl | 1.00[1] | 1.08 | 0.72 |
| Polyethylene Oxide POLYOX ® WSR-301 | ad 150.00 | 115.68 | 77.12 |
| Magnesium Stearate | 1.50 | 1.50 | 1.00 |
| Total core | 150.00 | 150.00 | 100.00 |

| Shell | Target mg/unit | Formulation (mg/unit) | Formulation (weight-%) |
|---|---|---|---|
| Oxycodone HCl | 10.00 | 10.58 | 4.23 |
| Buprenorphine HCl | 3.00[1] | 3.23 | 1.29 |
| Polyethylene Oxide POLYOX ® WSR N-10 | ad 250.00 | 234.69 | 93.88 |
| Magnesium Stearate | 1.50 | 1.50 | 0.60 |
| Total shell | 250.00 | 250.00 | 100.00 |

[1]expressed as equivalent amount of buprenorphine base

TABLE 9.2

| Core + Shell | Target mg/unit | Weight ratios | |
|---|---|---|---|
| Oxycodone HCl | 40.00 | Weight ratio oxycodone HCl$_{core}$/ oxycodone HCl$_{shell}$ | 3 |
| Buprenorphine HCl | 4.00[1] | Weight ratio buprenorphine HCl$_{core}$/ buprenorphine HCl$_{shell}$ | 0.33 |
| | | Weight ratio oxycodone$_{total}$/ buprenorphine$_{total}$ | 10 |
| Total weight core + shell | 400.00 | Weight ratio core/shell | 0.6 |

[1]expressed as equivalent amount of buprenorphine base

The processing steps to manufacture tablets of Example 9 correspond to the process of manufacture (steps 1 to 17) as described for Example 5.

Figure 9:
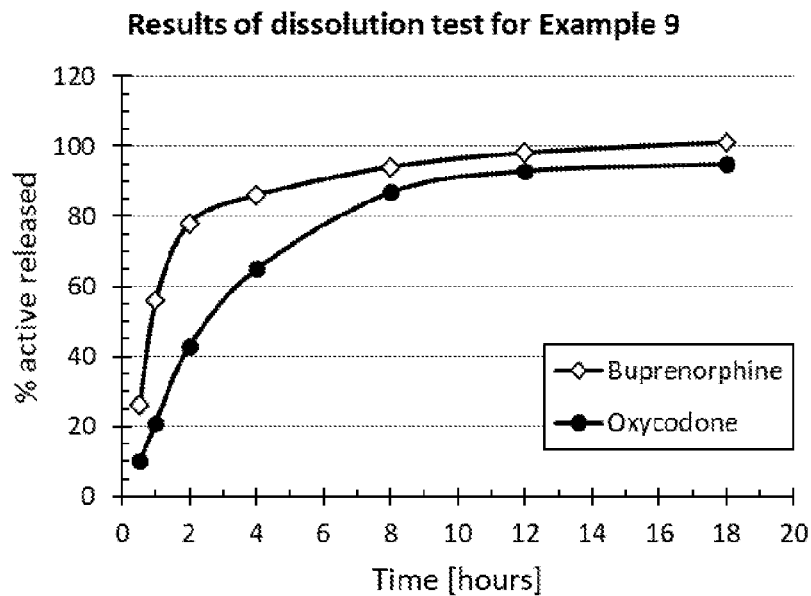
FIG. 9 is a graph depicting the results of the in vitro dissolution test of tablets according to Example 9.

The results of the in vitro dissolution testing of tablets of Example 9 are shown in Table 9.3 and in FIG. 9. The indicated values are an average of three measurements.

TABLE 9.3

| In vitro dissolution results for Example 9 | | | | | | | |
|---|---|---|---|---|---|---|---|
| Dissolution time [hours] | 0.5 | 1 | 2 | 4 | 8 | 12 | 18 |
| % oxycodone HCl released | 10 | 21 | 43 | 65 | 87 | 93 | 95 |
| % buprenorphine HCl released | 26 | 56 | 78 | 86 | 94 | 98 | 101 |

| | Weight (mg) | Thickness (mm) | Diameter (mm) |
|---|---|---|---|
| Core tablet | 147.2 | 4.04 | 7.12 |
| Core-Shell tablet before caring | 393.4 | 5.82 | 9.47 |
| Core-Shell tablet after curing | 391.3 | 6.32 | 9.23 |

Example 10

In Example 10, tablets comprising oxycodone hydrochloride and buprenorphine hydrochloride both in the core and in the shell and having the composition as shown in Tables 10.1 and 10.2 were prepared.

TABLE 10.1

| Core | Target mg/unit | Formulation (mg/unit) | Formulation (weight-%) |
|---|---|---|---|
| Oxycodone HCl | 60.00 | 63.48 | 33.74 |
| Buprenorphine HCl | 5.00[1] | 5.38 | 2.69 |
| Polyethylene Oxide POLYOX® WSR-301 | ad 200.00 | 131.14 | 65.57 |
| Total core | 200.00 | 200.00 | 100.00 |

| Shell | Target mg/unit | Formulation (mg/(unit) | Formulation (weight-%) |
|---|---|---|---|
| Oxycodone HCl | 20.00 | 21.16 | 3.85 |
| Buprenorphine HCl | 15.00[1] | 16.13 | 2.93 |
| Polyethylene Oxide POLYOX® WSR N-10 | ad 550.00 | 512.71 | 93.22 |
| Total shell | 550.00 | 550.00 | 100.00 |

[1]expressed as equivalent amount of buprenorphine base

TABLE 10.2

| Core + Shell | Target mg/unit | Weight ratios | |
|---|---|---|---|
| Oxycodone HCl | 80.00 | Weight ratio oxycodone HCl$_{core}$/ oxycodone HCl$_{shell}$ | |
| Buprenorphine HCl | 20.00[1] | Weight ratio buprenorphine HCl$_{core}$/ buprenorphine HCl$_{shell}$ Weight ratio oxycodone$_{total}$/ buprenorphine$_{total}$ | 0.33 |
| Total weight core + shell | 750.00 | Weight ratio core/shell | 0.36 |

[1]expressed as equivalent amount of buprenorphine base

The processing steps to manufacture tablets of Example 10 were as follows: Preparation of core blend:
1. Polyethylene oxide (POLYOX® WSR-301) was weighed and transferred into a 13 mm×100 mm glass test tube. An individual tube was used for each preparation.
2. The actives were weighed and transferred into the tube of step 1.
3. The materials in the tube were vortexed at high speed for 10 seconds to yield the core blend.

Preparation of shell blend:
4. Polyethylene oxide (POLYOX® WSR N-10) was weighed and transferred into a 13 mm×100 mm glass test tube. An individual tube was used for each preparation.
5. The actives were weighed and transferred into the tube of step 4.
6. The materials in the tube were vortexed at high speed for 10 seconds to yield the shell blend.

Preparation of Core Tablet:
7. The core blend was discharged onto a weighing paper (tapping the tube with a spatula 5 to dispense as much of the core blend as possible).
8. A Manesty Type F3 tablet press was setup with 5/16 inch round flat tooling.
9. The core blend was transferred into the die and compressed with upper punch penetration dial set at 24 to yield the core tablet.

Preparation of core-shell tablet(s)
10. A Manesty Type F3 tablet press was set up with 12 mm round, bevel edge, shallow concave tooling.
11. An amount of 250 mg±5 mg of the shell blend was discharged onto a weighing paper and transferred into the die.
12. The core tablet of step 9 was placed into the center of the die containing the indicated amount of the shell blend.
13. The remaining amount of the shell blend was discharged onto the same weighing paper (tapping the tube with a spatula to dispense as much of the shell blend as possible) and transferred into the die to cover the sides and the top of the core tablet.
14. Subsequently the shell blend was compressed with upper punch penetration dial set at 30±1 to yield the core-shell tablet.
15. Steps 1 to 14 were repeated to yield several core-shell tablets.

Curing
16. For curing, core-shell tablets were placed on a mesh screen and cured in a preheated gravity-flow convection oven at a temperature of 70° C. for 30 minutes.

Figure 10:
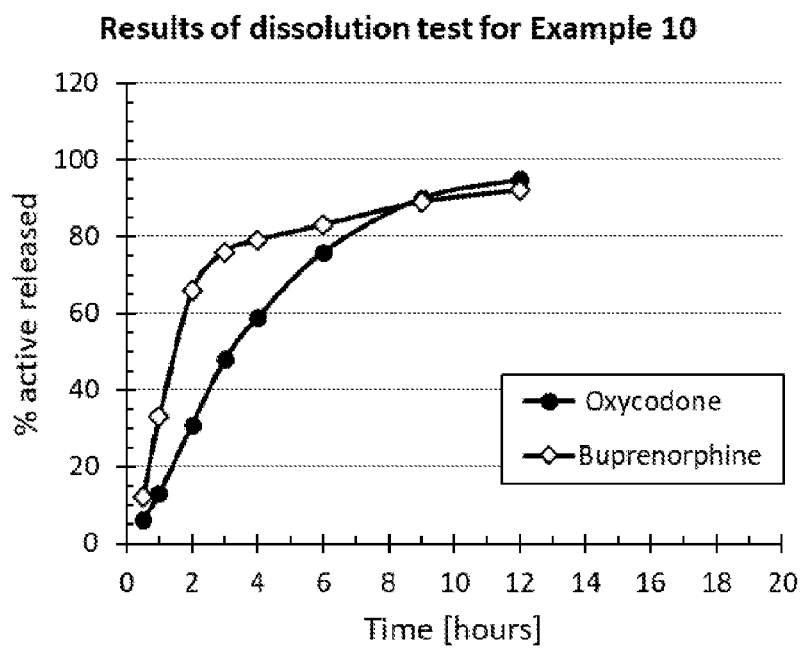
FIG. 10 is a graph depicting the results of the in vitro dissolution test of tablets according to Example 10.

The results of the in vitro dissolution testing of tablets of Example 10 are shown in Table 10.3 and in FIG. 10. The indicated values are an average of three measurements.

TABLE 10.3

| In vitro dissolution results for Example 10 | | | | | | | | |
|---|---|---|---|---|---|---|---|---|
| Dissolution time [hours] | 0.5 | 1 | 2 | 3 | 4 | 6 | 9 | 12 |
| % oxycodone HCl released | 6 | 13 | 31 | 48 | 59 | 76 | 90 | 95 |
| % buprenorphine HCl released | 12 | 33 | 66 | 76 | 79 | 83 | 89 | 92 |

| | Weight (mg) | Thickness (mm) |
|---|---|---|
| Core tablet | 196.5 | 3.81 |
| Core-Shell tablet before curing | 741.7 | 6.15 |
| Core-Shell tablet after curing | NT | 6.63 |

Example 11

In Example 11, tablets comprising oxycodone hydrochloride and buprenorphine hydrochloride both in the core and in the shell and having the composition as shown in Tables 11.1 and 11.2 were prepared.

TABLE 11.1

| Core | Target mg/unit | Formulation (g/unit) | Formulation (weight-%) |
|---|---|---|---|
| Oxycodone HCl | 7.50 | 7.93 | 5.29 |
| Buprenorphine HCl | 1.00[1] | 1.08 | 0.72 |
| Polyethylene Oxide POLYOX ® WSR-301 | ad 150.00 | 140.99 | 93.90 |
| Total core | 350.00 | 150.00 | 100.00 |

| Shell | Target mg/unit | Formulation (mg/unit) | Formulation (weight-%) |
|---|---|---|---|
| Oxycodone HOE | 2.50 | 2.64 | 0.48 |
| Buprenorphine ACl | 1.00[1] | 1.08 | 0.20 |
| Polyethylene Oxide POLYOX ® WSR N-10 | ad 550.00 | 546.28 | 99.32 |
| Total shell | 550.00 | 550.00 | 100.00 |

[1]expressed as equivalent amount of buprenorphine base

TABLE 11.2

| Core + Shell | Target mg/unit | Weight ratios | |
|---|---|---|---|
| Oxycodone HCl | 10.00 | Weight ratio oxycodone $HCl_{core}$/oxycodone $HCl_{shell}$ | 3 |
| Buprenorphine HCl | 2.00[1] | Weight ratio buprenorphine $HCl_{core}$/buprenorphine $HCl_{shell}$ | 1 |
| | | Weight ratio $oxycodone_{total}$/$buprenorphine_{total}$ | 5 |
| Total weight core + shell | 700.00 | Weight ratio core/shell | 0.27 |

[1]expressed as equivalent amount of buprenorphine base

The processing steps to manufacture tablets of Example 11 correspond to the process of manufacture (steps 1 to 16) as described for Example 10, with the following particulars:

In step 9, the upper punch penetration dial set at 26; and in step 14, the upper punch penetration dial set at 28/29.

Figure 11:
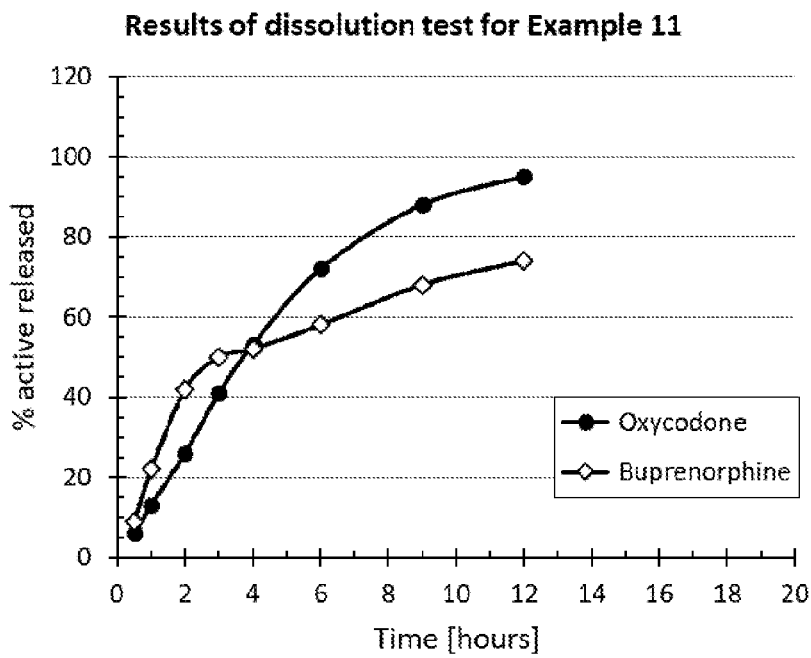
FIG. 11 is a graph depicting the results of the in vitro dissolution test of tablets according to Example 11.

The results of the in vitro dissolution testing of tablets of Example 11 are shown in Table 11.3 and in FIG. 11. The indicated values are an average of three measurements.

TABLE 11.3

| In vitro dissolution results for Example 11 | | | | | | | | |
|---|---|---|---|---|---|---|---|---|
| Dissolution time [hours] | 0.5 | 1 | 2 | 3 | 4 | 6 | 9 | 12 |
| % oxycodone HCl released | 6 | 13 | 26 | 41 | 53 | 72 | 88 | 95 |
| % buprenorphine HCl released | 9 | 22 | 42 | 50 | 52 | 58 | 68 | 74 |

| | Weight (mg) | Thickness (mm) |
|---|---|---|
| Core tablet | 147.3 | 3.06 |
| Core-Shell tablet before curing | 692.8 | 5.94 |
| Core-Shell tablet after curing | NT | 6.58 |

NT = Not Tested

Example 12

In Example 12, tablets comprising oxycodone hydrochloride and buprenorphine hydrochloride both in the core and in the shell and having the composition as shown in Tables 12.1 and 12.2 were prepared.

TABLE 12.1

| Core | Target mg/unit | Formulation (mg/unit)[1] | Formulation (weight-%) |
|---|---|---|---|
| Oxycodone HCl | 30.00 | 31.74 | 21.16 |
| Buprenorphine HCl | 1.50[2] | 1.61 | 1.07 |
| Polyethylene Oxide POLYOX ® WSR-301 | ad 150.00 | 116.65 | 77.77 |
| Total core | 150.00 | 150.00 | 100.00 |

| Shell | Target mg/unit | Formulation (mg/unit)[1] | Formulation (weight-%) |
|---|---|---|---|
| Oxycodone HCl | 10.00 | 10.58 | 4.23 |
| Buprenorphine HCl | 4.50[2] | 4.84 | 1.94 |
| Polyethylene Oxide POLYOX ® WSR N-10 | ad 250.00 | 234.58 | 93.83 |
| Total shell | 250.00 | 250.00 | 100.00 |

[1]In order to compensate for loss of material during handling, an overage of +7% was used for manufacturing individual tablets.
[2]expressed as equivalent amount of buprenorphine base

TABLE 12.2

| Core + Shell | Target mg/unit | Weight ratios | |
|---|---|---|---|
| Oxycodone HCl | 40.00 | Weight ratio oxycodone $HCl_{core}$/oxycodone $HCl_{shell}$ | 3 |
| Buprenorphine HCl | 6.00[1] | Weight ratio buprenorphine $HCl_{core}$/buprenorphine $HCl_{shell}$ | 0.33 |
| | | Weight ratio $oxycodone_{total}$/$buprenorphine_{total}$ | 6.67 |
| Total weight core + shell | 400.00 | Weight ratio core/shell | 0.6 |

[1]expressed as equivalent amount of buprenorphine base

The processing steps to manufacture tablets of Example 12 were as follows:

Preparation of core blend:
1. Polyethylene oxide (POLYOX® WSR-301) was weighed and transferred into a 13 mm×100 mm glass test tube. An individual tube was used for each preparation.

2. The active(s) were weighed and transferred into the tube of step 1.
3. The materials in the tube were vortexed at high speed for 10 seconds to yield the core blend.

Preparation of shell blend:
4. Polyethylene oxide (POLYOX® WSR N-1) was weighed and transferred into a 13 mm×100 mm glass test tube. An individual tube was used for each preparation.
5. The active(s) were weighed and transferred into the tube of step 4.
6. The materials in the tube were vortexed at high speed for 10 seconds to yield the shell blend.

Preparation of core tablet:
7. The core blend was discharged onto a weighing paper (tapping the tube with a spatula to dispense as much of the core blend as possible).
8. A Carver tablet press was setup with 9/32, round concave tooling.
9. The core blend was transferred into the die and compressed by applying a compression force of 1000-1200 lbs to yield the core tablet.

Preparation of Core-Shell Tablet(s)
10. A Carver tablet press was set up with 3/8, round concave tooling.
11. An amount of 115 mg±5 mg of the shell blend was discharged onto a weighing paper and transferred into the die.
12. The core tablet of step 9 was placed into the center of the die containing the indicated amount of the shell blend.
13. The remaining amount of the shell blend was discharged onto the same weighing paper (tapping the tube with a spatula to dispense as much of the shell blend as possible) and transferred into the die to cover the sides and the top of the core tablet.
14. Subsequently the shell blend was compressed by applying a compression force of 1800-2000 lbs to yield the core-shell tablet.
15. Steps 1 to 14 were repeated to yield several core-shell tablets.

Figure 12:
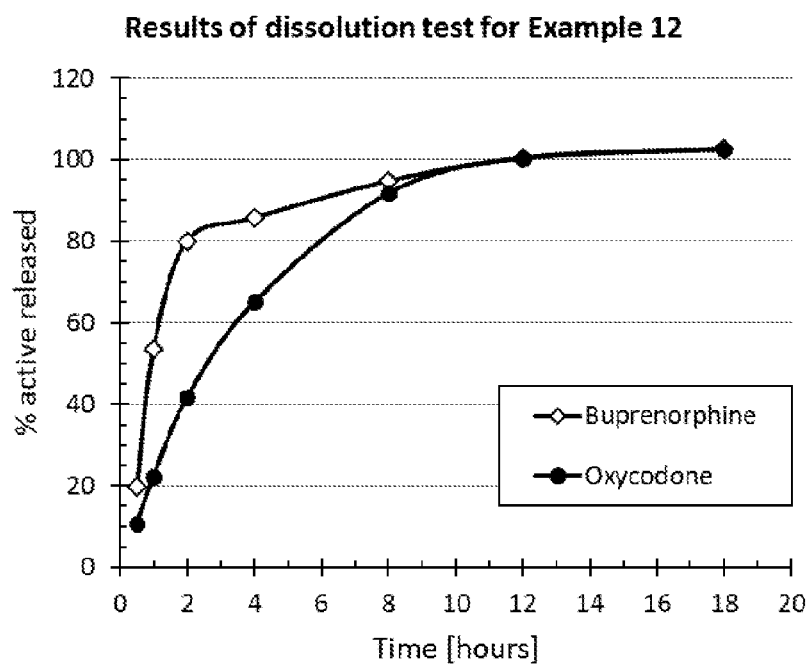
FIG. 12 is a graph depicting the results of the in vitro dissolution test of tablets according to Example 12.

The results of the in vitro dissolution testing of tablets of Example 12 are shown in Table 12.3 and in FIG. 12. The indicated values are an average of three measurements.

TABLE 12.3

In vitro dissolution results for Example 12

| Dissolution time [hours] | 0.5 | 1 | 2 | 4 | 8 | 12 | 18 |
|---|---|---|---|---|---|---|---|
| % oxycodone HCl released | 11 | 22 | 42 | 65 | 92 | 100 | 102 |
| % buprenorphine HCl released | 20 | 54 | 80 | 86 | 95 | 100 | 103 |

| | Weight (mg) |
|---|---|
| Core tablet | 147.1 |
| Core-Shell tablet | 394.1 |

Example 13

In Example 13, tablets comprising oxycodone hydrochloride in the core and buprenorphine hydrochloride in the shell and having the composition as shown in Tables 13.1 and 13.2 were prepared.

TABLE 13.1

| Core | Target mg/unit | Formulation (mg/unit)[1] | Formulation (weight-%) |
|---|---|---|---|
| Oxycodone HCl | 30.00 | 31.74 | 21.16 |
| Buprenorphine HCl | 0.00 | 0.00 | 0.00 |
| Polyethylene Oxide POLYOX® WSR-301 | ad 150.00 | 118.26 | 78.84 |
| Total core | 130.00 | 150.00 | 100.00 |

| Shell | Target mg/unit | Formulation (mg/unit) | Formulation (weight-%) |
|---|---|---|---|
| Oxycodone HCl | 0.00 | 0.00 | 0.00 |
| Buprenorphine HCl | 7.50[2] | 8.06 | 3.22 |
| Polyethylene Oxide POLYOXO WSR N-10 | ad 250.00 | 241.94 | 96.78 |
| Total shell | 250.00 | 250.00 | 100.00 |

[1]In order to compensate for loss of material during handling, an overage of +7% was used for manufacturing individual tablets.
[2]expressed as equivalent amount of buprenorphine base

TABLE 13.2

| Core + Shell | Target mg/unit | Weight ratios | |
|---|---|---|---|
| Oxycodone HCl | 30.00 | | |
| Buprenorphine HCl | 7.50[1] | | |
| | | Weight ratio oxycodone$_{total}$/ buprenorphine$_{total}$ | 4 |
| Total weight core + shell | 400.00 | Weight ratio core/shell | 0.6 |

[1]expressed as equivalent amount of buprenorphrine base

The processing steps to manufacture tablets of Example 13 correspond to the process of manufacture (steps 1 to 15) as described for Example 12.

Figure 13:
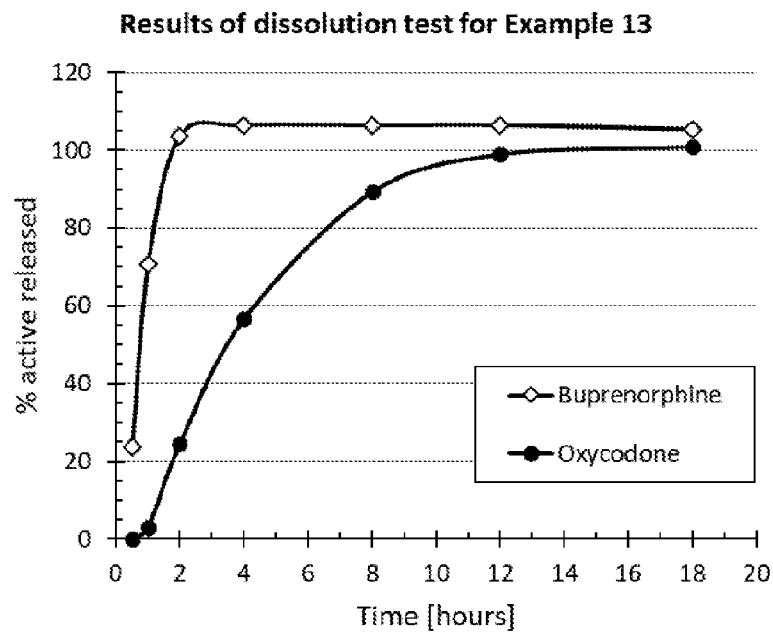
FIG. 13 is a graph depicting the results of the in vitro dissolution test of tablets according 30 to Example 13.

The results of the in vitro dissolution testing of tablets of Example 13 are shown in Table 13.3 and in FIG. 13. The indicated values are an average of three measurements.

TABLE 13.3

In vitro dissolution results for Example 13

| Dissolution time [hours] | 0.5 | 1 | 2 | 4 | 8 | 12 | 18 |
|---|---|---|---|---|---|---|---|
| % oxycodone HCl released | 0 | 3 | 25 | 57 | 89 | 99 | 108 |
| % buprenorphine HCl released | 24 | 71 | 104 | 106 | 106 | 106 | 106 |

| | Weight (mg) |
|---|---|
| Core tablet | 146.6 |
| Core-Shell tablet | 393.1 |

Example 14

In Example 14, tablets comprising buprenorphine hydrochloride in the core and oxycodone hydrochloride both in the core and in the shell, and having the composition as shown in Tables 14.1 and 14.2 were prepared.

TABLE 14.1

| Core | Target mg/unit | Formulation (mg/unit)[1] | Formulation (weight-%) |
|---|---|---|---|
| Oxycodone HCl | 21.00 | 22.22 | 14.81 |
| Buprenorphine HCl | 10.00[2] | 10.75 | 7.17 |
| Polyethylene Oxide POLYOX ® WSR-301 | ad 150.00 | 17.03 | 78.02 |
| Total core | 150.00 | 150.00 | 100.00 |

| Shell | Target mg/unit | Formulation (mg/unit) | Formulation (weight-%) |
|---|---|---|---|
| Oxycodone HCl | 19.00 | 20.10 | 8.04 |
| Buprenorphine HCl | 0.00 | 0.00 | 0.00 |
| Polyethylene Oxide POLYOX ® WSR N-10 | ad 250.00 | 229.90 | 91.96 |
| Total shell | 250.00 | 250.00 | 100.00 |

[1]In order to compensate for loss of material during handling, an overage of +7% was used for manufacturing individual tablets.
[2]expressed as equivalent amount of buprenorphine base

TABLE 14.2

| Core + Shell | Target mg/unit | Weight ratios | |
|---|---|---|---|
| Oxycodone HCl | 40.00 | Weight ratio oxycodone $HCl_{core}$/oxycodone $HCl_{shell}$ | 1.11 |
| Buprenorphine HCl | 10.00[1] | | |
| | | Weight ratio oxycodone$_{total}$/buprenorphine$_{total}$ | 4 |
| Total weight core + shell | 400.00 | Weight ratio core/shell | 0.6 |

[1]expressed as equivalent amount of buprenorphine base

The processing steps to manufacture tablets of Example 14 correspond to the process of manufacture (steps 1 to 15) as described for Example 12.

Figure 14:
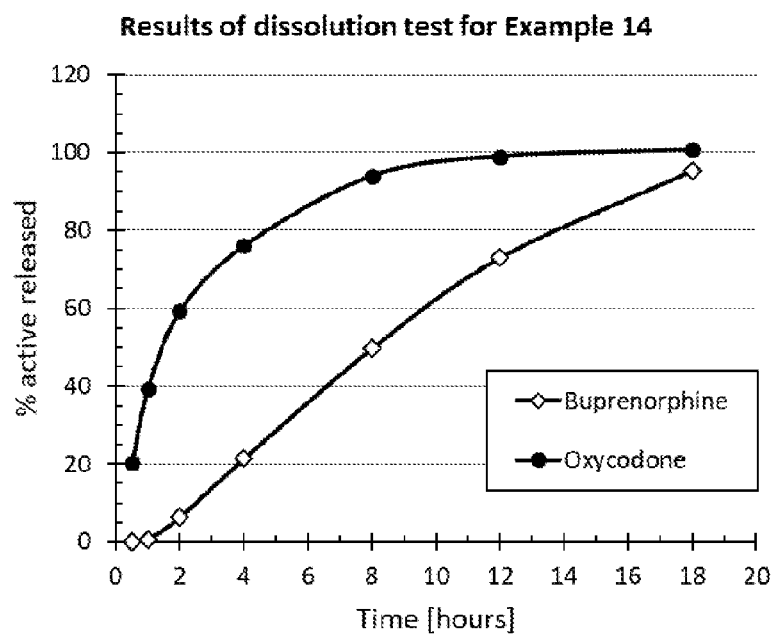
FIG. 14 is a graph depicting the results of the in vitro dissolution test of tablets according to Example 14.

The results of the in vitro dissolution testing of tablets of Example 14 are shown in Table 14.3 and in FIG. 14. The indicated values are an average of three measurements.

TABLE 14.3

In vitro dissolution results for Example 14

| Dissolution time [hours] | 0.5 | 1 | 2 | 4 | 8 | 12 | 18 |
|---|---|---|---|---|---|---|---|
| % oxycodone HCl released | 20 | 39 | 59 | 76 | 94 | 99 | 101 |
| % buprenorphine HCl released | 0 | 1 | 6 | 21 | 50 | 73 | 95 |

| | Weight (mg) |
|---|---|
| Core tablet | 146.0 |
| Core-Shell tablet | 393.0 |

Example 15

In Example 15, core tablets comprising buprenorphine hydrochloride and oxycodone hydrochloride were prepared and coated with an active-free polyethylene oxide shell. The resulting core-shell tablets have the composition as shown in Tables 15.1 and 15.2.

TABLE 15.1

| Core | Target mg/unit | Formulation (mg/unit)[1] | Formulation (weight-%) |
|---|---|---|---|
| Oxycodone HCl | 30.00 | 31.74 | 21.16 |
| Buprenorphine HCl | 10.00[2] | 10.75 | 7.17 |
| Polyethylene Oxide POLYOXI WSR-301 | ad 130.00 | 107.51 | 71.67 |
| Total core | 150.00 | 150.00 | 100.00 |

| Shell | Target mg/unit | Formulation (mg/unit)[1] | Formulation (weight-%) |
|---|---|---|---|
| Polyethylene Oxide POLYOX ® WSR N-10 | 250.00 | 20.00 | 100.00 |
| Total shell | 250.00 | 250.00 | 100.00 |

[1]In order to compensate for loss of material during handling, an overage of +7% was used for manufacturing individual tablets.
[2]expressed as equivalent amount of buprenorphine base

TABLE 15.2

| Core + Shell | Target mg/unit | Weight ratios | |
|---|---|---|---|
| Oxycodone HCl | 30.00 | | |
| Buprenorphine HCl | 10.00[2] | | |
| | | Weight ratio oxycodone$_{total}$/buprenorphine$_{total}$ | 3 |
| Total weight core + shell | 400.00 | Weight ratio core/shell | 0.6 |

[2]expressed as equivalent amount of buprenorphine base

The processing steps to manufacture tablets of Example 15 correspond to the process of manufacture (steps 1 to 15) as described for Example 12, with the exception that step 5 was omitted (i.e., no active(s) were added to the polyethylene oxide).

Figure 15:
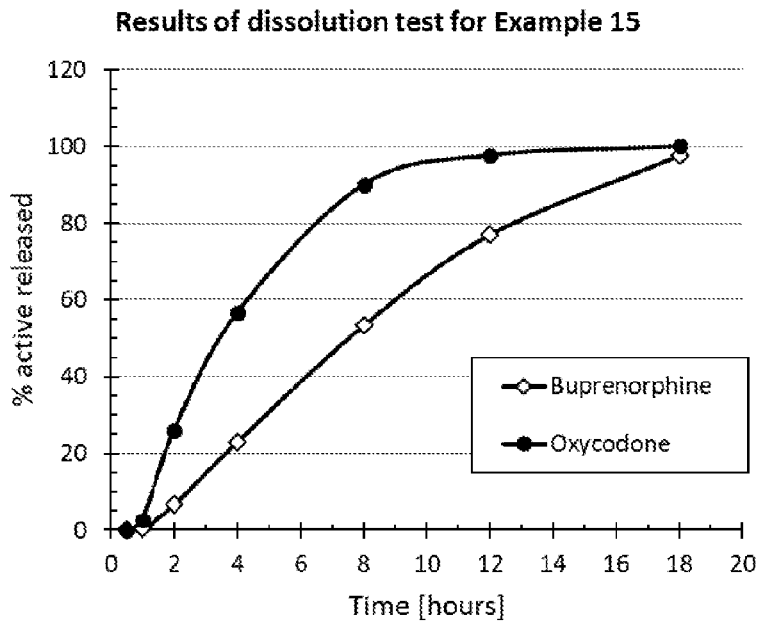
FIG. 15 is a graph depicting the results of the in vitro dissolution test of tablets according to Example 15.
Figure 16:
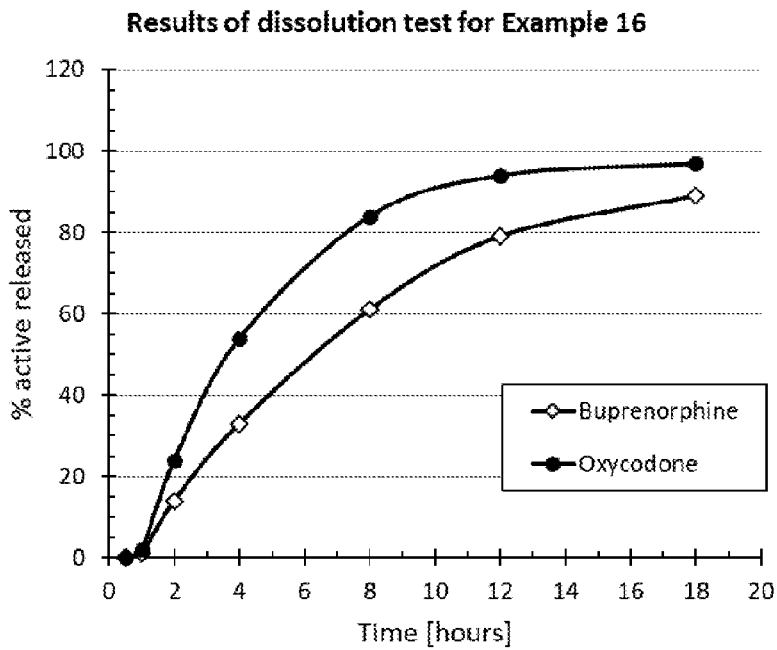
FIG. 16 is a graph depicting the results of the in vitro dissolution test of tablets according to Example 16.
Figure 17:
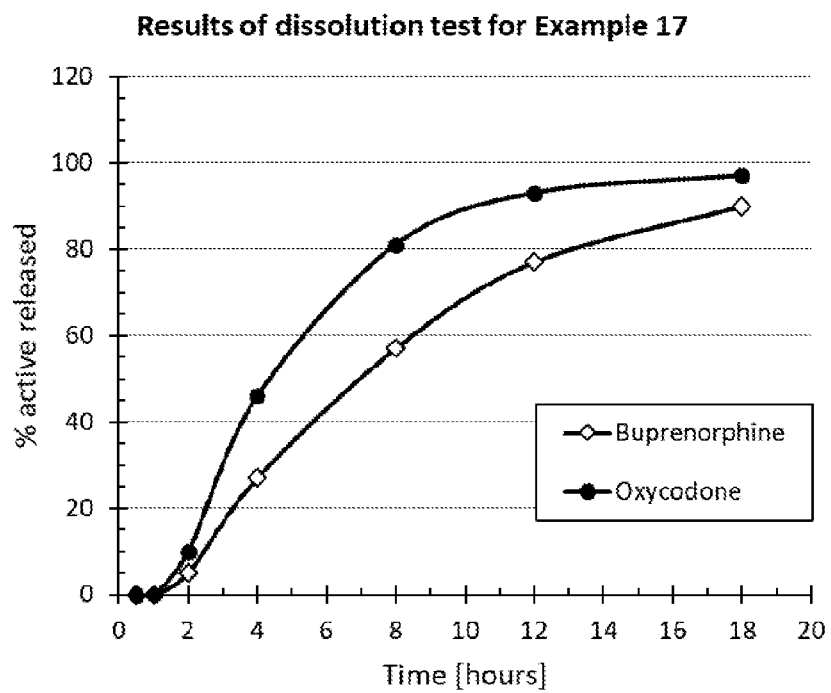
FIG. 17 is a graph depicting the results of the in vitro dissolution test of tablets according to Example 17.
Figure 18:
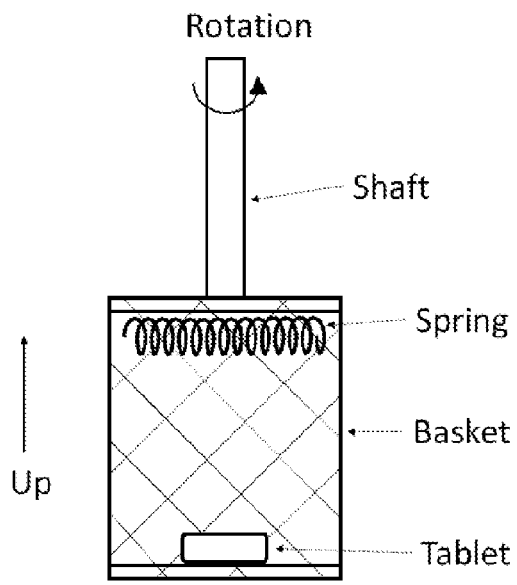
FIG. 18 is a schematic drawing of a USP basket equipped with a retaining spring placed in the upper part of the basket (above the tablet).
Figure 19:
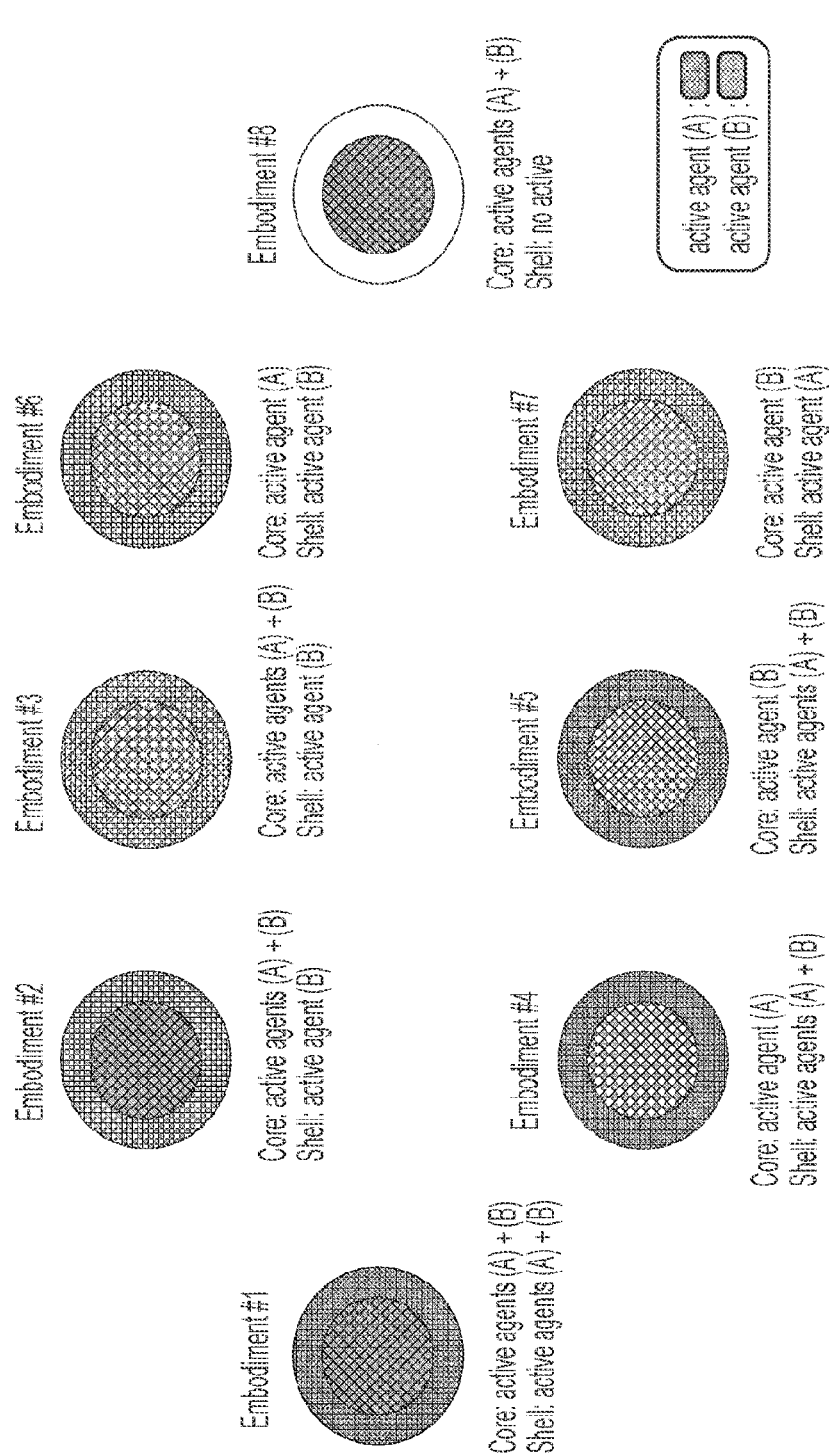
FIG. 19 is a schematic drawing illustrating core-shell structures of embodiments #1 to 10 #8.

The results of the in vitro dissolution testing of tablets of Example 15 are shown in Table 15.3 and in FIG. 15. The indicated values are an average of three measurements.

TABLE 15.3

In vitro dissolution results for Example 15

| Dissolution time [hours] | 0.5 | 1 | 2 | 4 | 8 | 12 | 18 |
|---|---|---|---|---|---|---|---|
| % oxycodone HCl released | 0 | 3 | 26 | 57 | 90 | 98 | 100 |
| % buprenorphine HCl released | 0 | 0 | 7 | 23 | 53 | 77 | 98 |

| | Weight (mg) |
|---|---|
| Core tablet | 145.6 |
| Core-Shell tablet | 391.2 |

Examples 16-17

In Examples 16 and 17, core tablets comprising buprenorphine hydrochloride and oxycodone hydrochloride were prepared and coated with an active-free polyethylene oxide shell.

The tablets have the composition as shown in Table 16.1 (for Example 16) and Table 17.1 (for Example 17).

TABLE 16.1

| Core | Target mg/unit | Formulation (mg/unit) | Formulation (weight-%) | Formulation (mg/batch) |
|---|---|---|---|---|
| Oxycodone HCl | 10.00 | 10.58 | 7.05 | 359.7 |
| Buprenorphine HCl | 0.50[1] | 0.54 | 0.36 | 18.3 |
| Polyethylene Oxide POLYOX® WSR-301 PP | ad 150.00 | 137.38 | 91.59 | 4671 |
| Magnesium Stearate | 1.50 | 1.50 | 1.00 | 51 |
| Total core | 150.00 | 150.00 | 100.00 | 5100.0 |

| Shell | Target mg/unit | Formulation (mg/unit) | Formulation (weight-%) |
|---|---|---|---|
| Polyethylene Oxide POLYOX® WSR N-10 | 250.00 | 250.00 | 100.00 |
| Total shell | 250.00 | 250.00 | 100.00 |
| Total weight core + shell | 400.00 | 400.00 | |

[1]expressed as equivalent amount of buprenorphine base

TABLE 17.1

| Core | Target mg/unit | Formulation (mg/unit) | Formulation (weight-%) | Formulation (mg/batch) |
|---|---|---|---|---|
| Oxycodone HCl | 10.00 | 10.58 | 7.05 | 359.7 |
| Buprenorphine HCl | 0.50[1] | 0.54 | 0.36 | 18.3 |
| Polyethylene Oxide POLYOX® WSR-301 FP | ad 150.00 | 137.38 | 91.59 | 4671 |
| Magnesium Stearate | 1.50 | 3.50 | 1.00 | 51 |
| Total core | 150.00 | 150.00 | 100.00 | 5100.0 |

| Shell | Target mg/unit | Formulation (mg/unit) | Formulation (weight-%) |
|---|---|---|---|
| Polyethylene Oxide POLYOX® WSR N-10 | 550.00 | 550.00 | 100.00 |
| Total shell | 550.00 | 550.00 | 100.00 |
| Total weight core + shell | 700.00 | 700.00 | |

[1]expressed as equivalent amount of buprenorphine base

The processing steps to manufacture the tablets of Examples 16 and 17 were as follows: Preparation of core tablets
The core tablets of Example 16 and 17 were manufactured in a 5100 mg batch as follows:
1. Add approximately half of the PEO into the 16 qt V-blender.
2. Mix a portion of PEO into the container of oxycodone HCl and manually mix for approximately 1 minute.
3. Screen the material from Step 2 through a 30-mesh screen while loading into the blender.
4. Mix a portion of PEO into the container of buprenorphine HCl and manually mix for approximately 1 minute.
5. Screen the material from Step 4 through a 30-mesh screen while loading into the blender.
6. Add the remaining PEO and mix for 5 minutes with the I-bar ON.
7. Add the magnesium stearate (screened through 30-mesh screen) and mix for 1 minute (no I-bar).
8. Discharge the blend.
9. Setup the Kilian tablet press (16 stations) with 9/32 inch round, standard concave tooling.
10. Add some blend to the hopper and adjust tablet parameters.
11. Compress the blend to target and collect tablets.

Preparation of core-shell tablet(s)
1. A Carver Press was set up with round concave tooling (size 3/8 inch round concave for Example 16 and size 12 mm round shallow concave with beveled edges for Example 17).
2. Polyethylene oxide (POLYOX® WSR N-10) was weighed.
3. Approximately 46% of the amount of polyethylene oxide of step 2 was transferred into the die.
4. A core tablet was placed into the center of the die containing the indicated partial amount of polyethylene oxide.
5. The remaining amount of polyethylene oxide was transferred into the die to cover the sides and the top of the core tablet.
6. Subsequently the polyethylene oxide was compressed by applying a compression force of 2000 lbs to yield the core-shell tablet.
7. Steps 1 to 6 were repeated to yield several core-shell tablets.

The results of the in vitro dissolution testing of (1) core tablets, (2) tablets of Example 16 and (3) tablets of Example 17 are shown in Table 16.2, 16.3 and 17.2, respectively. The indicated values are an average of three measurements.

TABLE 16.2

In vitro dissolution results for core tablets of Example 16/17

| Dissolution time [hours] | 0.5 | 1 | 2 | 4 | 8 | 12 | 18 |
|---|---|---|---|---|---|---|---|
| % oxycodone HCl released | 17 | 27 | 44 | 66 | 92 | 100 | 102 |
| % buprenorphine HCl released | 9 | 16 | 26 | 44 | 74 | 91 | 97 |

TABLE 16.3

In vitro dissolution results for Example 16

| Dissolution time [hours] | 0.5 | 1 | 2 | 4 | 8 | 12 | 18 |
|---|---|---|---|---|---|---|---|
| % oxycodone HCl released | 0 | 2 | 24 | 54 | 84 | 94 | 97 |
| % buprenorphine HCl released | 0 | 1 | 14 | 33 | 61 | 79 | 89 |

TABLE 17.2

In vitro dissolution results for Example 17

| Dissolution time [hours] | 0.5 | 1 | 2 | 4 | 8 | 12 | 18 |
|---|---|---|---|---|---|---|---|
| % oxycodone HCl released | 0 | 0 | 10 | 46 | 81 | 93 | 97 |
| % buprenorphine HCl released | 0 | 0 | 5 | 27 | 57 | 77 | 90 |

Having now fully described this disclosure, it will be understood by those of ordinary skill in the art that the same can be performed within a wide and equivalent range of conditions, formulations and other parameters without affecting the scope of the disclosure or any embodiment thereof.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

The invention claimed is:

1. A solid oral extended release dosage form comprising a core-shell structure comprising an active agent (A) and an active agent (B), wherein the active agent (A) is an opioid agonist, and the active agent (B) comprises a different opioid agonist, wherein the different opioid agonist is buprenorphine, and wherein the core-shell structure does not include an opioid antagonist;
   wherein the core-shell structure comprises
   (1) a core comprising a first matrix formulation, the first matrix formulation comprising at least one active agent comprising the active agent (A), or a first combination of the active agent (A) and the active agent (B); and
   (2) a shell encasing the core and consisting of a second matrix formulation, the second matrix formulation comprising at least one active agent comprising the active agent (B), or a second combination of the active agent (A) and the active agent (B); wherein the weight ratio of the first matrix formulation to the second matrix formulation is from about 1:10 to about 4:1,
   wherein each of the first matrix formulation and the second matrix formulation comprises at least one material selected from the group consisting of at least one polyethylene oxide, alkylcelluloses, cellulose ethers, waxes, shellacs, gums, acrylic resins, polyacrylates, polymethacrylates, and mixtures thereof,
   wherein when the first matrix formulation and the second matrix formulation comprise the active agent (A), a weight ratio of the active agent (A) in the first matrix formulation to the active agent (A) in the second matrix formulation is 1:50 to 50:1,
   wherein when the first matrix formulation and the second matrix formulation comprise the active agent (B), a weight ratio of the active agent (B) in the first matrix formulation to the active agent (B) in the second matrix formulation is 1:50 to 50:1,
   and wherein an amount of buprenorphine released from the dosage form, as measured by an in-vitro dissolution in a US Pharmacopeia Apparatus 1 at 100 rpm in 900 ml simulated gastric fluid without enzymes at 37.0° C., meets at least one of the following criteria:
   the amount of buprenorphine released from the dosage form at 1 hour is from 20 wt % to 75 wt %;
   the amount of buprenorphine released from the dosage form at 2 hours is from 40 wt % to 100 wt %;
   the amount of buprenorphine released from the dosage form at 4 hours is from 45 wt % to 100 wt %; or
   the amount of buprenorphine released from the dosage form at 8 hours is from 50 wt % to 100 wt %.

2. The solid oral extended release dosage form of claim 1, wherein the dosage form comprises a total amount of active agent (A) and a total amount of active agent (B), wherein at least 90 wt % of the total amount of active agent (A) and at least 90 wt % of the total amount of active agent (B) are contained in said first matrix formulation and/or said second matrix formulation.

3. The solid oral extended release dosage form of claim 1, comprising the at least one material that is selected from the group consisting of polyethylene oxides having, based on rheological measurements, an average molecular weight of from 100,000 g/mol to 900,000 g/mol, polyethylene oxides having, based on rheological measurements, an average molecular weight of from 1,000,000 g/mol to 8,000,000 g/mol, acrylic and methacrylic acid polymers and copolymers, ethylcellulose, hydroxyalkylcelluloses, carboxyalkylcelluloses, waxes selected from natural and synthetic waxes, fatty acids, fatty alcohols, hydrogenated vegetable oil, and mixtures thereof.

4. The solid oral extended release dosage form of claim 1, wherein the first matrix formulation comprises from about 20 wt % to about 99 wt % of said at least one material based on the weight of the first matrix formulation.

5. The solid oral extended release dosage form of claim 1, wherein the second matrix formulation comprises from about 20 wt % to about 99 wt % of said at least one material based on the weight of the second matrix formulation.

6. The solid oral extended release dosage form of claim 1, wherein the at least one polyethylene oxide has, based on rheological measurements, an average molecular weight of from 100,000 g/mol to 900,000 g/mol.

7. The solid oral extended release dosage form of claim 1, wherein the first matrix formulation comprises from about 20 wt % to about 99 wt % of said at least one polyethylene oxide based on the weight of the first matrix formulation.

8. The solid oral extended release dosage form of claim 7, wherein the at least one polyethylene oxide of the first matrix formulation has, based on rheological measurements, an average molecular weight of from 1,000,000 g/mol to 8,000,000 g/mol; and the at least one polyethylene oxide of the second matrix formulation has, based on rheological measurements, an average molecular weight of from 100,000 g/mol to 600,000 g/mol.

9. The solid oral extended release dosage form of claim 1, wherein the first matrix formulation comprises from about 50 wt % to about 95 wt % of said at least one polyethylene oxide based on the weight of the first matrix formulation, and
   the second matrix formulation comprises from about 60 wt % to about 99 wt % of said at least one polyethylene oxide based on the weight of the second matrix formulation.

10. The solid oral extended release dosage form of claim 8, wherein
   the first matrix formulation comprises from about 50 to about 95 wt % based on the weight of the first matrix formulation of the at least one polyethylene oxide, which has, based on rheological measurements, an average molecular weight of from 2,000,000 g/mol to 8,000,000 g/mol, and
   the second matrix formulation comprises from about 60 wt % to about 99 wt % based on the weight of the second matrix formulation of the at least one polyethylene oxide, which has, based on rheological measurements, an average molecular weight of from 100,000 g/mol to 300,000 g/mol.

11. The solid oral extended release dosage form of claim 1, wherein the dosage form comprises a plurality of particles, each particle comprising said core-shell structure.

12. The solid oral extended release dosage form of claim 1, wherein the first matrix formulation and the second matrix formulation have a CIE L*A*B* value within 10% of each other.

13. A method of treating or preventing pain comprising administering to a patient identified in need thereof a solid oral extended release dosage form according to claim 1, wherein active agent (A) is an opioid agonist.

\* \* \* \* \*